(12) United States Patent
Libbus et al.

(10) Patent No.: US 9,409,025 B2
(45) Date of Patent: *Aug. 9, 2016

(54) CARDIAC RHYTHM MANAGEMENT DEVICE WITH NEURAL SENSOR

(75) Inventors: Imad Libbus, St. Paul, MN (US);
Andrew P. Kramer, Marine on St. Croix, MN (US); Julia Moffitt, Iowa City, IA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1346 days.

This patent is subject to a terminal disclaimer.

(21) Appl. No.: 12/840,449

(22) Filed: Jul. 21, 2010

(65) Prior Publication Data

US 2010/0286741 A1 Nov. 11, 2010

Related U.S. Application Data

(63) Continuation of application No. 10/992,320, filed on Nov. 18, 2004, now Pat. No. 7,769,450.

(51) Int. Cl.
*A61N 1/36* (2006.01)
*A61N 1/362* (2006.01)

(52) U.S. Cl.
CPC .......... *A61N 1/3627* (2013.01); *A61N 1/36114* (2013.01); *A61N 1/36117* (2013.01)

(58) Field of Classification Search
CPC ... A61N 1/36; A61N 1/3627; A61N 1/36114; A61N 1/36117
USPC ........................................... 607/9, 17, 22, 23
See application file for complete search history.

(56) References Cited

U.S. PATENT DOCUMENTS 4,201,219 A * 5/1980 Bozal Gonzalez .............. 607/22
4,791,931 A 12/1988 Slate
(Continued)

FOREIGN PATENT DOCUMENTS

EP 0481583 A2 4/1992
EP 0688578 A1 12/1995
(Continued)

OTHER PUBLICATIONS

"U.S. Appl. No. 10/992,320, Examiner Interview Summary mailed Feb. 20, 2009", 2 pgs.
(Continued)

*Primary Examiner* — Christopher A Flory
(74) *Attorney, Agent, or Firm* — Schwegman Lundberg & Woessner, P.A.

(57) ABSTRACT

Various aspects of the present subject matter relate to a device. In various embodiments, the device comprises at least one port adapted to connect at least one lead, a CRM functions module connected to the port and adapted to provide at least one CRM function using the lead, a neural function module, and a controller connected to the CRM functions module and the neural function module. The at least one CRM function includes a function to provide an electrical signal to the lead to capture cardiac tissue. The neural function module includes a signal processing module connected to the port and adapted to receive and process a nerve traffic signal from the lead into a signal indicative of the nerve traffic. The controller is adapted to implement a CRM therapy based on the signal indicative of the nerve traffic. Other aspects are provided herein.

12 Claims, 15 Drawing Sheets

(56) References Cited

U.S. PATENT DOCUMENTS

| | | | |
|---|---|---|---|
| 5,111,815 A | 5/1992 | Mower | |
| 5,190,035 A | 3/1993 | Salo et al. | |
| 5,199,428 A | 4/1993 | Obel et al. | |
| 5,203,326 A | 4/1993 | Collins | |
| 5,243,980 A | 9/1993 | Mehra | |
| 5,318,592 A | 6/1994 | Schaldach | |
| 5,324,316 A | 6/1994 | Schulman et al. | |
| 5,330,507 A | 7/1994 | Schwartz | |
| 5,356,425 A | 10/1994 | Bardy et al. | |
| 5,437,285 A | 8/1995 | Verrier et al. | |
| 5,507,784 A | 4/1996 | Hill et al. | |
| 5,522,854 A | 6/1996 | Ideker et al. | |
| 5,540,730 A | 7/1996 | Terry, Jr. et al. | |
| 5,578,061 A | 11/1996 | Stroetmann et al. | |
| 5,658,318 A * | 8/1997 | Stroetmann et al. | 607/6 |
| 5,690,681 A | 11/1997 | Geddes et al. | |
| 5,700,282 A | 12/1997 | Zabara | |
| 5,913,882 A | 6/1999 | King | |
| 5,916,239 A | 6/1999 | Geddes et al. | |
| 6,006,134 A | 12/1999 | Hill et al. | |
| 6,073,048 A | 6/2000 | Kieval et al. | |
| 6,134,470 A | 10/2000 | Hartlaub | |
| 6,161,042 A | 12/2000 | Hartley et al. | |
| 6,164,284 A | 12/2000 | Schulman et al. | |
| 6,178,349 B1 | 1/2001 | Kieval | |
| 6,178,351 B1 | 1/2001 | Mower | |
| 6,195,585 B1 | 2/2001 | Karunasiri et al. | |
| 6,240,316 B1 | 5/2001 | Richmond et al. | |
| 6,371,922 B1 | 4/2002 | Baumann et al. | |
| 6,393,316 B1 * | 5/2002 | Gillberg et al. | 600/515 |
| 6,400,982 B2 | 6/2002 | Sweeney et al. | |
| 6,421,557 B1 | 7/2002 | Meyer | |
| 6,473,644 B1 | 10/2002 | Terry, Jr. et al. | |
| 6,522,926 B1 | 2/2003 | Kieval et al. | |
| 6,535,763 B1 | 3/2003 | Hiebert et al. | |
| 6,587,725 B1 | 7/2003 | Durand et al. | |
| 6,611,713 B2 | 8/2003 | Schauerte | |
| 6,622,041 B2 | 9/2003 | Terry, Jr. et al. | |
| 6,628,987 B1 * | 9/2003 | Hill et al. | 607/9 |
| 6,658,287 B1 | 12/2003 | Litt et al. | |
| 6,695,885 B2 | 2/2004 | Schulman et al. | |
| 6,738,667 B2 | 5/2004 | Deno et al. | |
| 6,804,561 B2 | 10/2004 | Stover | |
| 6,934,583 B2 * | 8/2005 | Weinberg et al. | 607/9 |
| 6,937,896 B1 * | 8/2005 | Kroll | 607/9 |
| 6,993,388 B2 | 1/2006 | Bullinga | |
| 7,020,521 B1 * | 3/2006 | Brewer et al. | 607/14 |
| 7,123,961 B1 | 10/2006 | Kroll et al. | |
| 7,149,574 B2 | 12/2006 | Yun et al. | |
| 7,194,313 B2 * | 3/2007 | Libbus | 607/42 |
| 7,225,016 B1 | 5/2007 | Koh | |
| 7,277,761 B2 | 10/2007 | Shelchuk | |
| 7,640,057 B2 | 12/2009 | Libbus et al. | |
| 7,769,450 B2 * | 8/2010 | Libbus et al. | 607/17 |
| 8,131,362 B2 * | 3/2012 | Moffitt et al. | 607/9 |
| 2002/0042637 A1 | 4/2002 | Stover | |
| 2002/0058877 A1 | 5/2002 | Baumann et al. | |
| 2002/0068875 A1 | 6/2002 | Schroeppel et al. | |
| 2002/0107553 A1 | 8/2002 | Hill et al. | |
| 2002/0107557 A1 | 8/2002 | Edell et al. | |
| 2002/0165586 A1 | 11/2002 | Hill et al. | |
| 2003/0040774 A1 * | 2/2003 | Terry et al. | 607/2 |
| 2003/0045909 A1 | 3/2003 | Gross et al. | |
| 2003/0055461 A1 | 3/2003 | Girouard et al. | |
| 2003/0060848 A1 | 3/2003 | Kieval et al. | |
| 2003/0060857 A1 | 3/2003 | Perrson et al. | |
| 2003/0060858 A1 | 3/2003 | Kieval et al. | |
| 2003/0078623 A1 * | 4/2003 | Weinberg et al. | 607/9 |
| 2003/0100924 A1 | 5/2003 | Foreman et al. | |
| 2003/0114905 A1 | 6/2003 | Kuzma | |
| 2003/0158584 A1 | 8/2003 | Cates et al. | |
| 2003/0195578 A1 | 10/2003 | Perron et al. | |
| 2003/0212445 A1 | 11/2003 | Weinberg | |
| 2004/0019364 A1 | 1/2004 | Kieval et al. | |
| 2004/0131998 A1 | 7/2004 | Marom et al. | |
| 2004/0138517 A1 * | 7/2004 | Osorio et al. | 600/9 |
| 2004/0138579 A1 | 7/2004 | Deadwyler et al. | |
| 2004/0172075 A1 * | 9/2004 | Shafer et al. | 607/9 |
| 2004/0193231 A1 * | 9/2004 | David et al. | 607/48 |
| 2004/0199210 A1 * | 10/2004 | Shelchuk | 607/17 |
| 2004/0210261 A1 | 10/2004 | King et al. | |
| 2004/0215263 A1 | 10/2004 | Virag et al. | |
| 2005/0060001 A1 | 3/2005 | Singhal et al. | |
| 2005/0085864 A1 | 4/2005 | Schulman et al. | |
| 2005/0096705 A1 | 5/2005 | Pastore et al. | |
| 2005/0143779 A1 | 6/2005 | Libbus | |
| 2005/0143785 A1 | 6/2005 | Libbus | |
| 2005/0149126 A1 | 7/2005 | Libbus | |
| 2005/0149127 A1 | 7/2005 | Libbus | |
| 2005/0149128 A1 | 7/2005 | Heil, Jr. et al. | |
| 2005/0149129 A1 | 7/2005 | Libbus et al. | |
| 2005/0149130 A1 | 7/2005 | Libbus | |
| 2005/0149131 A1 * | 7/2005 | Libbus et al. | 607/9 |
| 2005/0149132 A1 | 7/2005 | Libbus | |
| 2005/0149133 A1 | 7/2005 | Libbus et al. | |
| 2005/0149143 A1 * | 7/2005 | Libbus et al. | 607/44 |
| 2005/0149155 A1 | 7/2005 | Scheiner et al. | |
| 2005/0149156 A1 | 7/2005 | Libbus et al. | |
| 2005/0261741 A1 * | 11/2005 | Libbus et al. | 607/3 |
| 2005/0288718 A1 * | 12/2005 | Sunagawa et al. | 607/9 |
| 2006/0074451 A1 * | 4/2006 | Chen et al. | 607/3 |
| 2006/0106428 A1 | 5/2006 | Libbus et al. | |
| 2006/0106429 A1 | 5/2006 | Libbus et al. | |
| 2006/0116737 A1 | 6/2006 | Libbus | |
| 2006/0135998 A1 | 6/2006 | Libbus et al. | |
| 2006/0167497 A1 | 7/2006 | Armstrong et al. | |
| 2006/0241697 A1 | 10/2006 | Libbus et al. | |
| 2006/0241725 A1 | 10/2006 | Libbus | |
| 2007/0021799 A1 | 1/2007 | Kieval et al. | |
| 2007/0142864 A1 | 6/2007 | Libbus et al. | |
| 2008/0167694 A1 | 7/2008 | Bolea et al. | |
| 2008/0228238 A1 | 9/2008 | Libbus | |
| 2010/0049281 A1 | 2/2010 | Libbus et al. | |

FOREIGN PATENT DOCUMENTS

| | | |
|---|---|---|
| EP | 0721786 A2 | 7/1996 |
| JP | 05-76609 A | 3/1993 |
| JP | 2002-534232 A | 10/2002 |
| JP | 200416333 A | 1/2004 |
| JP | 2004-523269 A | 8/2004 |
| WO | WO-02/053026 A2 | 7/2002 |
| WO | WO-2004/012814 A1 | 2/2004 |
| WO | WO-2004/036372 A2 | 4/2004 |
| WO | WO-2004041069 A2 | 5/2004 |
| WO | WO-2006/055436 A1 | 5/2006 |
| WO | WO-2006/055849 A1 | 5/2006 |
| WO | WO-2006/115868 A1 | 11/2006 |
| WO | WO-2006/115899 A1 | 11/2006 |
| WO | WO-2008/063396 A1 | 5/2008 |

OTHER PUBLICATIONS

"U.S. Appl. No. 10/992,320, Examiner Interview Summary mailed Apr. 30, 2009", 2 pgs.

"U.S. Appl. No. 10/992,320, Final Office Action mailed Mar. 19, 2008", 8 pgs.

"U.S. Appl. No. 10/992,320, Non-Final Office Action mailed Sep. 25, 2009", 12 pgs.

"U.S. Appl. No. 10/992,320, Non-Final Office Action Mailed Sep. 28, 2007", 7 pgs.

"U.S. Appl. No. 10/992,320, Non-Final Office Action mailed Nov. 12, 2008", 9 pgs.

"U.S. Appl. No. 10/992,320, Notice of Allowance mailed Mar. 30, 2010", 4 pgs.

"U.S. Appl. No. 10/992,320, Notice of Allowance mailed Apr. 30, 2009", 6 pgs.

"U.S. Appl. No. 10/992,320, Notice of Allowance mailed May 12, 2009", 8 pgs.

"U.S. Appl. No. 10/992,320, Notice of Allowance mailed Sep. 2, 2009", 5 pgs.

"U.S. Appl. No. 10/992,320, Preliminary Amendment filed Nov. 18, 2004", 3 pgs.

(56) References Cited

OTHER PUBLICATIONS

"U.S. Appl. No. 10/992,320, Response filed Jul. 21, 2008 to Final Office Action mailed Mar. 19, 2008", 11 pgs.

"U.S. Appl. No. 10/992,320, Response filed Jan. 25, 2010 to Non-Final Office Action mailed Sep. 24, 2009", 15 pgs.

"U.S. Appl. No. 10/992,320, Response filed Feb. 12, 2009 to Non-Final Office Action mailed Nov. 12, 2008", 14 pgs.

"U.S. Appl. No. 10/992,320, Response filed Dec. 28, 2007 to Non-Final Office Action mailed Sep. 28, 2007", 11 pgs.

"European Application Serial No. 05825864.1, Minutes of Oral Proceedings mailed Dec. 15, 2009", 7 pgs.

"European Application Serial No. 05825864.1, Communication mailed Sep. 11, 2007", 6 pgs.

"European Application Serial No. 05825864.1, Office Action mailed May 19, 2008", 5 pgs.

"European Application Serial No. 05825864.1, Response filed Dec. 1, 2008 to Communication mailed May 19, 2008", 7 pgs.

"European Application Serial No. 05825864.1, Response filed Mar. 20, 2008 to Communication mailed Sep. 11, 2007", 12 pgs.

"European Application Serial No. 05825864.1, Summons to Attend Oral Proceedings mailed Jul. 9, 2009", 4 pgs.

"International Search Report and Written Opinion for Application No. PCT/US2005/040988, date mailed Mar. 27, 2006", 12 pgs.

"Japanese Application Serial No. 2007-543138, Amended Claims filed Nov. 12, 2008", (w/ English Translation of Amended Claims), 13 pgs.

Chapleau, M W, "Neuro-cardiovascular regulation: from molecules to man. Introduction.", *Annals of the New York Academy of Sciences*, 940, (Jun. 2001), xiii-xxii.

Chapleau, M. W., et al., "Contrasting effects of static and pulsatile pressure on carotid baroreceptor activity in dogs", *Circulation*, vol. 61, No. 5, (Nov. 1987), 648-658.

Chapleau, M. W., "Pulsatile activation of baroreceptors causes central facilitation of baroreflex", *American Journal Physiol Heart Circ Physiol*, (Jun. 1989), 256: H1735-H1741.

Diedrich, A, "Analysis of raw microneurographic recordings based on wavelet de-noising technique and classification algorithm: wavelet analysis in microneurography", *IEEE Transactions on Biomedical Engineering*, 50(1), (Jan. 2003), 41-50.

Hamdan, M. H., et al., "Effects of Resynchronization Therapy on Sympathetic Activity in Patients With Depressed Ejection Fraction and Intraventricular Conduction Delay Due to Ischemic or Idiopathic Dilated Cardiomyopathy", *Am. J. Cardol.*, 89, (2002), 1047-1051.

Li, M., et al., "Vagal nerve stimulation markedly improves long-term survival after chronic heart failure in rats", *Circulation*, 109(1), (2004), 120-124.

Libbus, I., et al., "Method and Apparatus for Synchronizing Neural Simulation to Cardiac Cycles", U.S. Appl. No. 11/099,141, filed Apr. 5, 2005, 36 pgs.

Libbus, I., et al., "System and Method for Closed-Loop Neural Stimulation", U.S. Appl. No. 10/992,319, filed Nov. 18, 2004, 50 pgs.

Sigurdsson, A., et al., "The Role of Neurohormonal Activation in Chronic Heart Failure and Postmyocardial Infarction", *American Heart Journal*, 132(1, Part 2), (Jul. 1996), 229-234.

Vanoli, E., et al., "Vagal Stimulation and Prevention of Sudden Death in Conscious Dogs With a Healed Myocardial Infarction", *Circulation Research*, 68(5), (May 1991), 1471-1481.

Wasmund, S. L., et al., "Effect of Atrial Fibrillation and an Irregular Ventricular Response on Sympathetic Nerve Activity in Human Subjects", *Circulation*, 107, (2003), 2011-2015.

Yanagiya, Y., et al., "Bionic epidural stimulation restores arterial pressure regulation during orthostasis", *J. Appl. Physiol*, 97(3), (Sep. 2004), 984-990.

"Japanese Application Serial No. 2007-543138, Response filed Dec. 20, 2011 to Office Action mailed Jun. 20, 2011", (w/ English Translation of Amended Claims), 15 pgs.

De Landsheere, D, et al., "Effect of spinal cord stimulation on regional myocardial perfusion assessed by positron emission tomography", *American Journal of Cardiology*, 69(14), (May 1, 1992), 1143-1149.

Farrehi, C, "Stimulation of the carotid sinus nerve in treatment of angina pectoris", *American Heart Journal*, 80(6), (Dec. 1970), 759-765.

Grassi, G., et al., "Baroreflex and non-baroreflex modulation of vagal cardiac control after myocardial infarction", *Am J Cardiol.*, 84(5), (Sep. 1, 1999), 525-529.

Henning, R. J., et al., Effects of autonomic nerve stimulation, asynchrony, and load on $dP/dt_{max}$ and on $dP/dt_{min}$. *American Journal of Physiology*, 260(4 Pt 2), (1991), H1290-H1298.

Ishise, H, et al., "Time course of sympathovagal imbalance and left ventricular dysfunction in conscious dogs with heart failure", *Journal of Applied Physiology*, 84(4), (Apr. 1998), 1234-1241.

Minisi, A J, et al., "Regional left ventricular deafferentation increases baroreflex sensitivity following myocardial infarction", *Cardiovasc Res.*, 58(1), (Apr. 1, 2003), 136-141.

Stanford, V., "Biosignals Offer Potential for Direct Interfaces and Health Monitoring", *IEEE Pervasive Computing*, (Jan.-Mar. 2004), 99-103.

"Japanese Application Serial No. 2007-543138, Office Action mailed Jun. 18, 2012", 5 pgs.

"Japanese Application Serial No. 2007-543138, Office Action mailed Jun. 22, 2011", 4 pgs.

\* cited by examiner

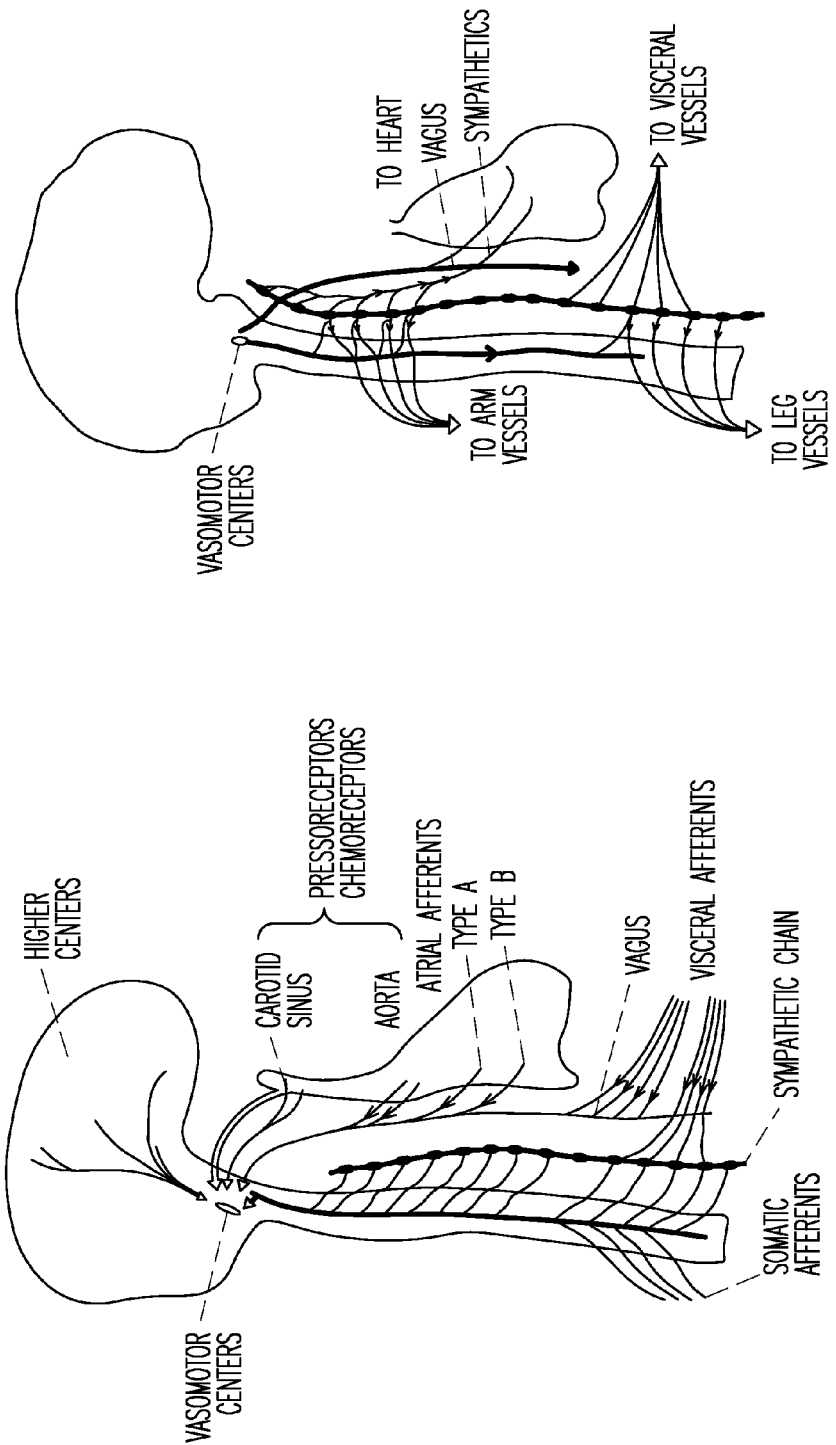

CARDIAC RHYTHM MANAGEMENT DEVICE WITH NEURAL SENSOR

CLAIM OF PRIORITY

This application is a continuation of and claims the benefit of priority under 35 U.S.C. §120 to U.S. patent application Ser. No. 10/992,320, filed on Nov. 18, 2004, now issued as U.S. Pat. No. 7,769,450, which is hereby incorporated by reference herein in its entirety.

CROSS REFERENCE TO RELATED APPLICATIONS

The following commonly assigned U.S. patent applications are related, and are herein incorporated by reference in their entirety: "Automatic Baroreflex Modulation Based on Cardiac Activity," Ser. No. 10/746,846, filed on Dec. 24, 2003, abandoned; and "System and Method for Closed-Loop Neural Stimulation," Ser. No. 10/992,319, filed on Nov. 18, 2004, published as U.S. 20060106429.

TECHNICAL FIELD

This application relates generally to neural stimulation systems and, more particularly, to systems, devices and methods for sensing nerve traffic and providing closed-loop cardiac stimulation based at least in part on sensed nerve traffic.

BACKGROUND

Examples of cardiac stimulators include implantable cardiac rhythm management (CRM) devices such as pacemakers, implantable cardiac defibrillators (ICDs), and implantable devices capable of performing pacing and defibrillating functions. CRM devices are implantable devices that provide electrical stimulation to selected chambers of the heart in order to treat disorders of cardiac rhythm. An implantable pacemaker, for example, is a CRM device that paces the heart with timed pacing pulses. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

A pressoreceptive region or field is capable of sensing changes in pressure, such as changes in blood pressure. Pressoreceptor regions are referred to herein as baroreceptors, which generally include any sensors of pressure changes. For example, baroreceptors transmit neural signals through afferent nerves and further include sensory nerve endings that are sensitive to the stretching of the vessel wall that results from increased blood pressure from within, and function as receptors of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, causing baroreflex inhibition of sympathetic nerve activity (SNA), activation of parasympathetic nerve activity, and a reduction in systemic arterial pressure. An increase in baroreceptor activity induces a reduction of SNA, which reduces blood pressure by decreasing peripheral vascular resistance.

SUMMARY

Various aspects of the present subject matter relate to a device. In various embodiments, the device comprises at least one port adapted to connect at least one lead, a CRM functions module connected to the port and adapted to provide at least one CRM function using the lead, a neural function module, and a controller connected to the CRM functions module and the neural function module. The at least one CRM function includes a function to provide an electrical signal to the lead to capture cardiac tissue. The neural function module includes a signal processing module connected to the port and adapted to receive and process a nerve traffic signal from the lead into a signal indicative of the nerve traffic. The controller is adapted to implement a CRM therapy based on the signal indicative of the nerve traffic.

Various aspects of the present subject matter relate to a system. In various embodiments, the system comprises means for sensing a nerve traffic signal, means for identifying at least one feature of the nerve traffic signal, and means for applying CRM therapy based on the at least one feature of the nerve traffic signal.

Various aspect of the present subject matter relate to a method. In various embodiments of the method, a nerve traffic signal is sensed, at least one feature of the nerve traffic signal is identified, and CRM therapy is applied based on the at least one feature of the nerve traffic signal.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIGS. 1A and 1B illustrate neural mechanisms for peripheral vascular control.

DETAILED DESCRIPTION

Figure 2B:
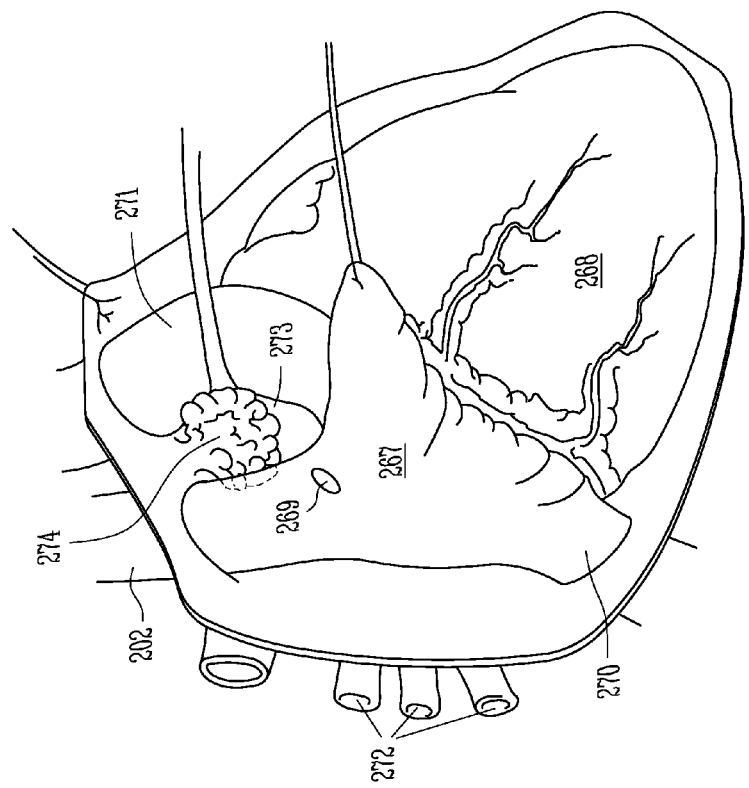
FIGS. 2A-2C illustrate a heart.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

A device is provided with at least one lead for use to perform CRM and neural sensing functions. The device is adapted to amplify, filter, record and analyze the target nerve activity, and use the resulting information to accurately and appropriately deliver CRM therapy such as cardiac resynchronization therapy (CRT), for example. Sympathetic nerve activity (SNA) has a low signal amplitude (1-10 µV), and relatively high noise amplitude. Various embodiments provide amplification to provide a gain within a range of approximately 1,000 to approximately 99,000, for example, and bandpass filtering to process neural traffic associated with SNA. Various embodiments provide bandpass filtering to pass frequencies within a range of approximately 30 Hz to approximately 3,000 Hz. Various embodiments use various subsets of these gain and frequency ranges. Various embodiments implement a noise reduction algorithm, such as a wavelet transform, for example.

By monitoring nerve traffic to deliver appropriate CRM therapy, the present subject matter provides a closed-loop neural stimulation system. A neural sensing lead is used to record nerve traffic from the peripheral nervous system, such as baroreceptors, afferent nerves and/or efferent nerves, to guide CRM therapy and to record physiologic parameters such as pressure for diagnostic purposes.

Nerve traffic adapts to long-term changes in activity, such that it can be difficult to determine nerve activity during long-term recordings. Therefore, various embodiments of the present subject matter perturb the physiologic system with a short stimulation burst, and the neural response to the stimulation burst, rather than the baseline activity, is used to determine neural receptor activity. In various embodiments, the CRM device perturbs the physiologic system using a transient stimulation of the myocardium, such as a premature stimulus to induce a change in pulse pressure, and the neural response to the stimulation is monitored to determine neural receptor sensitivity. Various embodiments adjust CRM therapy to account for long-term changes in receptor sensitivity, as determined by this technique. The data recorded with the neural sensing lead is monitored and used to guide CRM therapy. Some embodiments, for example, use nerve traffic at specific locations as a surrogate for certain physiological parameters, such as arterial pressure or blood gas levels. Various CRM device embodiments record, store, and track pulse pressure data to guide therapy, such as to improve cardiac resynchronization therapy (CRT). Other applications for the present subject matter include, but are not limited to, ventricular tachycardia (VT) and ventricular fibrillation (VF) detection, the detection and treatment of sleep apnea and dyspnea, and the detection and treatment of vasovagal syncope. Vasovagal relates to the action of the vagus nerve upon the blood vessels, and syncope relates to the loss of consciousness and postural tone caused by diminished cerebral blood flow.

Baroreceptors and chemoreceptors in the heart, great vessels and lungs transmit cardiac activity through vagal and sympathetic afferent fibers to the central nervous system. The nerve traffic sensor for the CRM device includes a lead placed in position to sense electrical signal corresponding to nerve traffic. Various embodiments use a lead placed in a baroreceptor field such as in the aorta, various embodiments use a lead placed in an efferent nerve pathway such as a cardiac fat pad, and various embodiments use a lead placed around a nerve trunk such as the aortic, carotid, and vagus nerves. According to various embodiments, the targeted nerve traffic corresponds to baroreceptors, and thus are useful to determine blood pressure. According to various embodiments, the targeted nerve traffic to be sensed corresponds to chemoreceptors, and thus are useful to determine blood gas concentrations.

A brief description of baroreflex and chemoreceptors is provided below, followed by various systems to provide CRM therapy with sensed nerve traffic feedback. CRT through biventricular pacing has been shown to improve cardiac function. CRT is enhanced by monitoring and adapting to changes in left ventricular pressure. Various CRM device embodiments use a nerve traffic sensor to monitor nerve traffic and indirectly deduce aortic pressure. Pressure sensors currently suffer from long-term drift, which makes it more difficult to monitor a patient's blood pressure over long periods of time; whereas recording nerve traffic with a neural sensor provides a stable way of monitoring blood pressure.

Baroreceptor and Chemoreceptor Physiology

A brief discussion of the physiology related to baroreceptors and chemoreceptors is provided to assist the reader with understanding this disclosure. This brief discussion introduces, the autonomic nervous system, baroreflex, and chemoreceptors.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Various embodiments of the present subject matter provide neural stimulation to affect the heart rate, blood pressure, vasodilation and vasoconstriction. The heart rate and force is increased when the sympathetic nervous system is stimulated, and is decreased when the sympathetic nervous system is inhibited (the parasympathetic nervous system is stimulated). Various embodiments detect nerve traffic as a surrogate parameter for another physiologic parameter, such as heart rate, blood pressure and the like. FIGS. 1A and 1B illustrate neural mechanisms for peripheral vascular control. FIG. 1A generally illustrates afferent nerves to vasomotor centers. An afferent nerve conveys impulses toward a nerve center. A vasomotor center relates to nerves that dilate and constrict blood vessels to control the size of the blood vessels. FIG. 1B generally illustrates efferent nerves from vasomotor centers. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system and/or inhibiting the sympathetic nervous system constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems. Additionally, sensing of nerve traffic for use as a surrogate parameter of a physiological parameter can depend on a number of physiological parameters. Various embodiments of the present subject matter perturb the physiological system with precisely located neural stimulation, and monitor the nerve traffic response to the stimulation.

A pressoreceptive region or field is capable of sensing changes in pressure, such as changes in blood pressure. Pressoreceptor regions are referred to herein as baroreceptors, which generally include any sensors of pressure changes. For example, baroreceptors include afferent nerves and further include sensory nerve endings that provide baroreceptor fields that are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, which excites the parasympathetic nervous system causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. Centrally mediated reflex pathways modulate cardiac rate, contractility and excitability. Baroreceptors and chemoreceptors in the heart, great vessels, and lungs, transmit neural signals reflective of cardiac activity through vagal and afferent fibers to the central nervous system. Thus, physiological parameters, such as systemic arterial pressure, can be determined based on nerve traffic. Such pressure information, for example, provides useful feedback information to guide CRM therapy such as CRT.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Afferent nerves can also be electrically stimulated to induce a baroreflex, which inhibits the sympathetic nerve activity and stimulates parasympathetic nerve activity. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptors are naturally stimulated by internal pressure and the stretching of vessel wall (e.g. arterial wall).

Some aspects of the present subject matter locally sense specific nerve endings in vessel walls rather than or in addition to afferent and/or efferent nerve trunks. For example, some embodiments sense baroreceptor sites or fields in the pulmonary artery. Some embodiments of the present subject matter involve sensing baroreceptor sites or nerve endings in the aorta, the chambers of the heart, some embodiments of the present subject matter involve sensing efferent pathways such as the fat pads of the heart, and some embodiments of the present subject matter involve stimulating an afferent nerve trunk, such as the vagus, carotid and aortic nerves. Various embodiments involve combinations of sensing nerve ending, sensing efferent nerve pathways and sensing afferent nerve pathways. Some embodiments sense nerve trunks using a cuff electrode, and some embodiments sense nerve trunks using an intravascular lead positioned in a blood vessel proximate to the nerve. Examples of afferent nerve trunks include the vagus, aortic and carotid nerves. Examples of efferent nerve trunks include the cardiac branches off the vagus nerve. Stimulation of efferent nerves such as these cardiac branches or the nerves in cardiac fat pads conveys nervous impulses to an effector, and thus do not use the baroreflex negative feedback of the central nervous system, which responds to nerve activity on afferent nerves with nerve activity on efferent nerves. Some embodiments sense neural traffic at any of the above-identified neural stimulation sites.

Figure 2A:
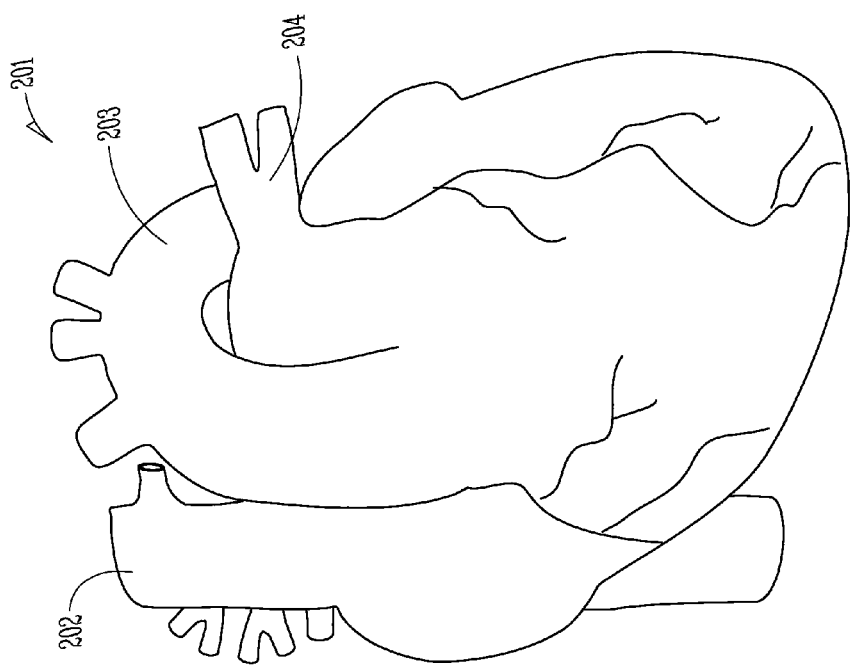
Figure 2C:
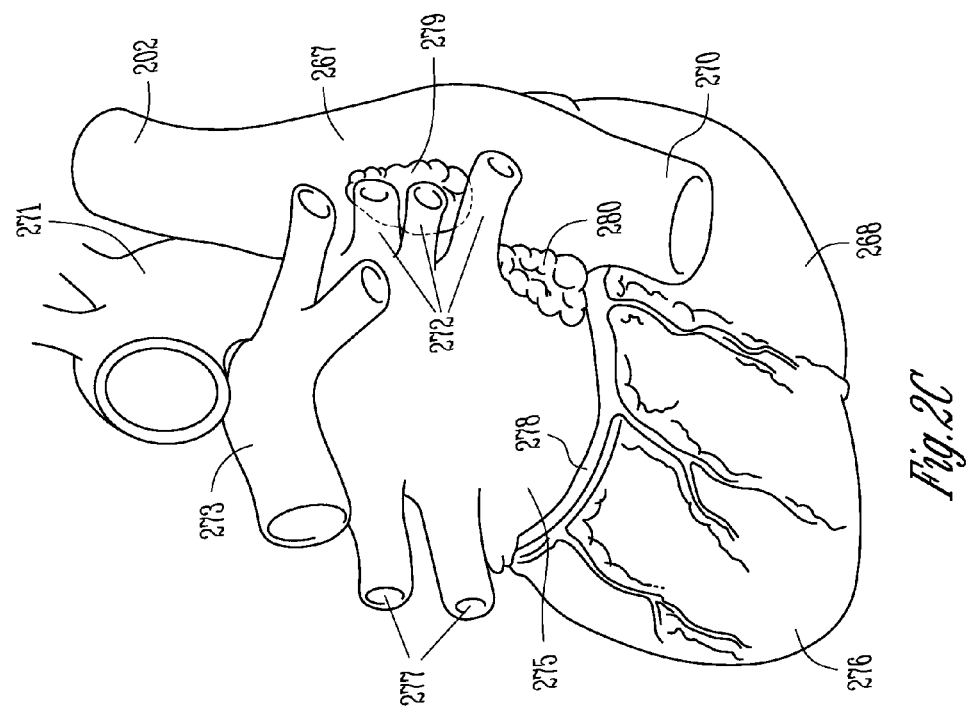

FIGS. 2A-2C illustrate a heart. As illustrated in FIG. 2A, the heart 201 includes a superior vena cava 202, an aortic arch 203, and a pulmonary artery 204, and is useful to provide a contextual relationship with the illustrations in FIGS. 3-5. As is discussed in more detail below, the pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. A portion of the pulmonary artery and aorta are proximate to each other. Various embodiments stimulate baroreceptors and/or sense neural activity by the baroreceptor in the aorta using a lead intravascularly positioned in the pulmonary artery. Thus, according to various aspects of the present subject matter, the baroreflex is stimulated and/or nerve activity is sensed in or around the pulmonary artery by at least one electrode intravascularly inserted into the pulmonary artery. In various embodiments, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a neural traffic sensor, with or without a baroreceptor stimulator, intravascularly into the pulmonary artery.

FIGS. 2B-2C illustrate the right side and left side of the heart, respectively, and further illustrate cardiac fat pads. FIG. 2B illustrates the right atrium 267, right ventricle 268, sinoatrial node 269, superior vena cava 202, inferior vena cava 270, aorta 271, right pulmonary veins 272, and right pulmonary artery 273. FIG. 2B also illustrates a cardiac fat pad 274 between the superior vena cava and aorta. Autonomic ganglia in the cardiac fat pad 274 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as the right pulmonary artery or superior vena cava, for example. FIG. 2C illustrates the left atrium 275, left ventricle 276, right atrium 267, right ventricle 268, superior vena cava 202, inferior vena cava 270, aorta 271, right pulmonary veins 272, left pulmonary vein 277, right pulmonary artery 273, and coronary sinus 278. FIG. 2C also illustrates a cardiac fat pad 279 located proximate to the right cardiac veins and a cardiac fat pad 280 located proximate to the inferior vena cava and left atrium. Autonomic ganglia in the fat pad 279 are stimulated and/or nerve traffic is sensed in some embodiments using an electrode screwed or otherwise inserted into the fat pad 279, and are stimulated and/or nerve traffic is sensed in some embodiments using an intravenously-fed lead proximately positioned to the fat pad in a vessel such as the right pulmonary artery 273 or right pulmonary vein 272, for example. Autonomic ganglia in the cardiac fat pad 280 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as the inferior vena cava 270 or coronary sinus or a lead in the left atrium 275, for example.

Figure 3:
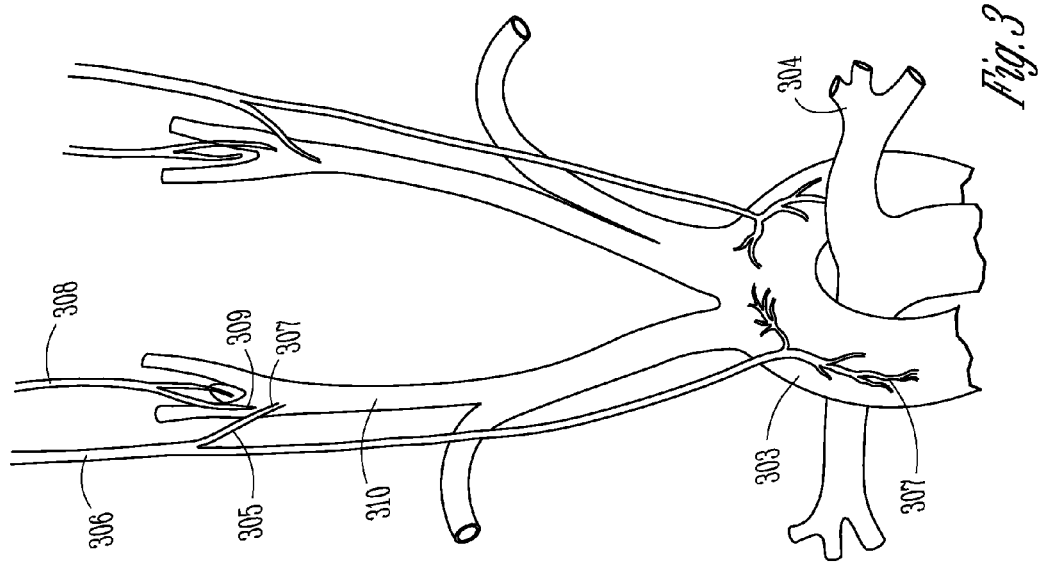
FIG. 3 illustrates baroreceptors and afferent nerves in the area of the carotid sinuses and aortic arch.

FIG. 3 illustrates baroreceptors in the area of the carotid sinus 305, aortic arch 303 and pulmonary artery 304. The aortic arch 303 and pulmonary artery 304 were previously illustrated with respect to the heart in FIG. 2A. As illustrated in FIG. 3, the vagus nerve 306 extends and provides sensory nerve endings 307 that function as baroreceptors in the aortic arch 303, in the carotid sinus 305 and in the common carotid artery 310. The glossopharyngeal nerve 308 provides nerve endings 309 that function as baroreceptors in the carotid sinus 305. These nerve endings 307 and 309, for example, are sensitive to stretching of the wall resulting from increased pressure from within. Activation of these nerve endings reduce pressure. Although not illustrated in the figures, the fat pads and the atrial and ventricular chambers of the heart also include baroreceptors. Cuffs have been placed around afferent nerve trunks, such as the vagal nerve, leading from baroreceptors to vasomotor centers to stimulate the baroreflex. According to various embodiments of the present subject matter, afferent nerve trunks can be stimulated and/or nerve traffic from the afferent nerve trunks can be sensed using a cuff or intravascularly-fed lead positioned in a blood vessel proximate to the afferent nerves.

Figure 5:
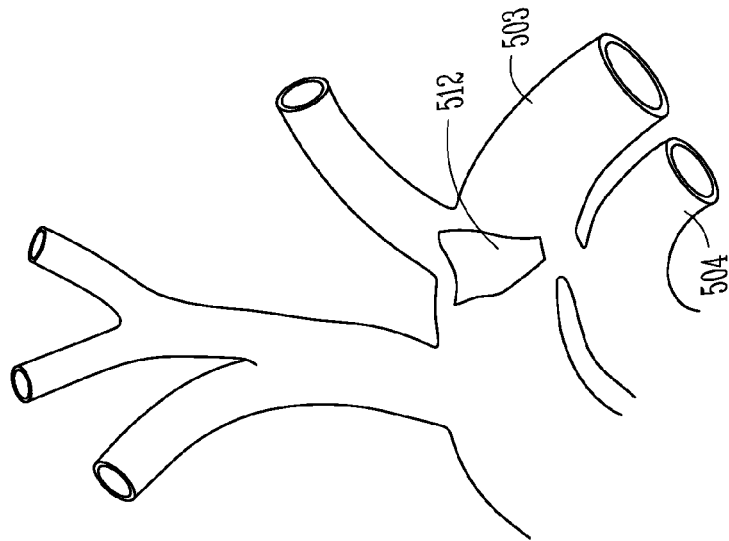
FIG. 5 illustrates baroreceptor fields in the aortic arch, the ligamentum arteriosum and the trunk of the pulmonary artery.
Figure 4:
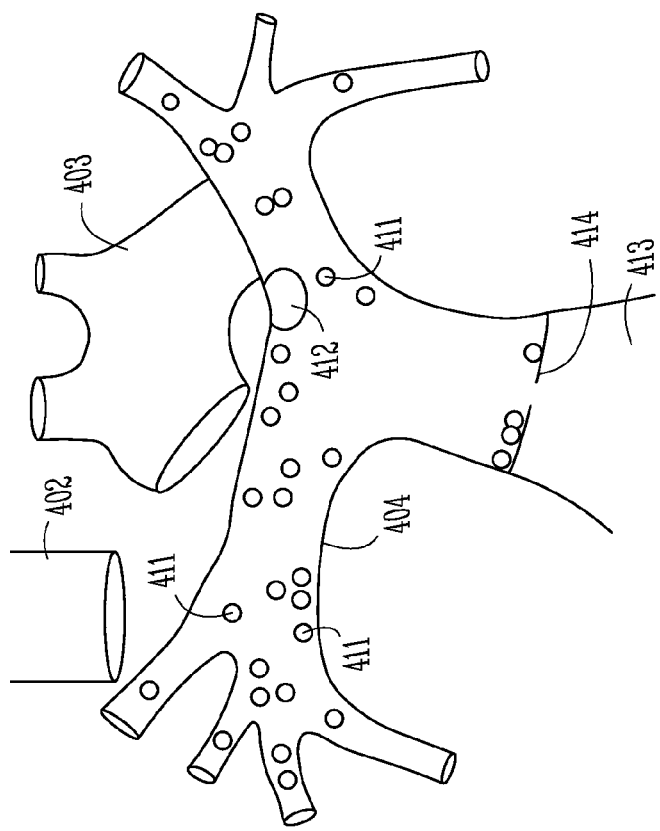
FIG. 4 illustrates baroreceptors in and around the pulmonary artery.

FIG. 4 illustrates baroreceptors in and around a pulmonary artery 404. The superior vena cava 402 and the aortic arch 403 are also illustrated. As illustrated, the pulmonary artery 404 includes a number of baroreceptors 411, as generally indicated by the dark area. Furthermore, a cluster of closely spaced baroreceptors is situated near the attachment of the ligamentum arteriosum 412. FIG. 4 also illustrates the right ventricle 413 of the heart, and the pulmonary valve 414 separating the right ventricle 413 from the pulmonary artery 404. According to various embodiments of the present subject matter, a lead is inserted through a peripheral vein and threaded through the tricuspid valve into the right ventricle, and from the right ventricle 413 through the pulmonary valve 414 and into the pulmonary artery 404 to stimulate baroreceptors and/or sense nerve traffic from the baroreceptors in and/or around the pulmonary artery. In various embodiments, for example, the lead is positioned to stimulate the cluster of baroreceptors and/or sense nerve traffic near the ligamentum arteriosum 412. FIG. 5 illustrates baroreceptor fields 512 in the aortic arch 503, near the ligamentum arteriosum and the trunk of the pulmonary artery 504. Some embodiments position the lead in the pulmonary artery to stimulate baroreceptor sites and/or sense nerve traffic in the aorta and/or fat pads, such as are illustrated in FIGS. 2B-2C.

Figure 6:
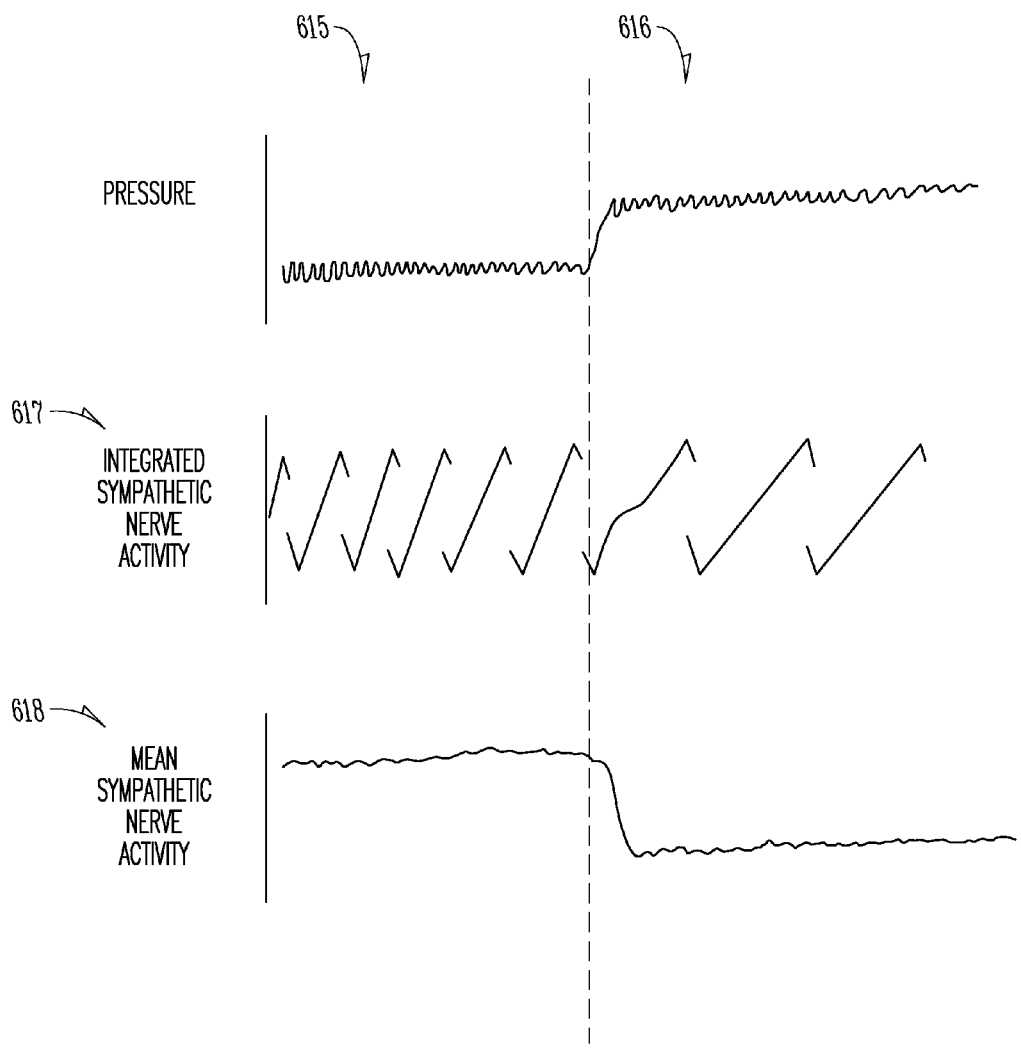
FIG. 6 illustrates an example of a neural response after perturbing a physiologic system.

FIG. 6 illustrates an example of a neural response after perturbing a physiologic system. In the illustration, pressure functions as an indicator for a physiologic system. The system is illustrated in a first low pressure condition 615 and a second high pressure condition 616. Nerve activity, illustrated at 617 and 618, changes between the two conditions.

The change may be rather transient in nature if the nervous system quickly adapts from the first to the second condition, or may be more sustained if the nervous system does not quickly adapt to the change in conditions. Regardless, an analysis of a sensed nerve traffic signal can extract or otherwise determine features of the signal indicative of the response. In the illustrated example, the waveform 617 associated with an integrated sympathetic nerve activity changes (e.g. change in slope and period of waveform) from the first to the second conditions. Additionally, the waveform 618 associated with a mean sympathetic nerve activity changes (e.g. a first level of nerve activity to a second level of nerve activity) from the first to the second conditions. The integrated sympathetic nerve activity and mean sympathetic nerve activity waveforms are provided as examples. Other ways of sensing changes in the neural traffic signals can be used.

Various embodiments of the present subject matter sense nerve traffic corresponding to chemoreceptors. The carotid and aortic bodies provide a concentration of cardiovascular chemoreceptors. The carotid body lies deep to the bifurcation of the common carotid artery or somewhat between the two branches. The carotid body is a small, flattened, oval structure, 2 to 5 mm in diameter, with a characteristic structure composed of epithelioid cells, which are in close relation to capillary sinusoids, and an abundance of nerve fibers. Surrounding the carotid body is a delicate fibrous capsule. It is part of the visceral afferent system of the body, containing chemoreceptor endings that respond to low levels of oxygen in the blood or high levels of carbon dioxide and lowered pH of the blood. It is supplied by nerve fibers from both the glossopharyngeal and vagus nerves.

The aortic bodies (glomera aortica) are chemoreceptors similar to the carotid bodies. Afferent fibers from the aortic bodies run in the right vagus and have cell bodies in the inferior ganglion. The supracardial bodies (aortic paraganglia) are also chemoreceptors with their afferent fibers in the left vagus and cell bodies in the inferior ganglion.

CRM Systems with Neural Traffic Feedback

Various embodiments of the present subject matter include stand-alone implantable CRM systems, and include implantable devices that have integrated NS and CRM components, and include systems with at least one implantable NS device and an implantable CRM device capable of communicating with each other either wirelessly or through a wire lead connecting the implantable devices. Although implantable systems are illustrated and discussed, various aspects and embodiments of the present subject matter can be implemented in external devices.

Figure 7:
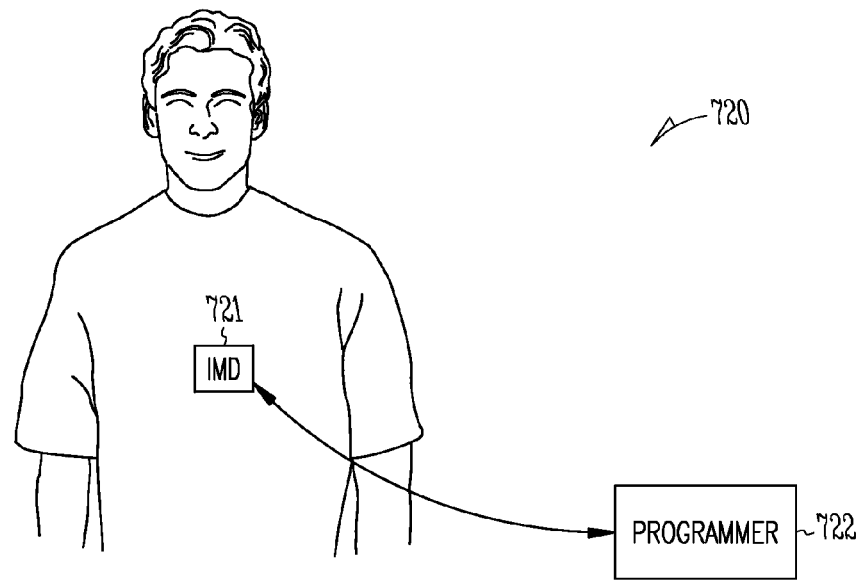
FIG. 7 illustrates a system including an implantable medical device (IMD) and a programmer, according to various embodiments of the present subject matter.

FIG. 7 illustrates a system 720 including an implantable medical device (IMD) 721 and a programmer 722, according to various embodiments of the present subject matter. Various IMD embodiments of the IMD 721 include CRM functions with neural sensing, and various embodiments further include neural stimulation. Examples of CRM devices include implantable pacemakers, implantable cardiac defibrillators (ICDs), implantable devices capable of performing pacing and defibrillating functions, and CRT devices. Implantable CRM devices provide electrical stimulation to selected chambers of the heart in order to treat disorders of cardiac rhythm. An implantable pacemaker, for example, is a CRM device that paces the heart with timed pacing pulses. The pacing pulses can be timed from other pacing pulses or sensed electrical activity. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output. Some embodiments provide neural stimulation to treat hypertension.

CRM functions can be improved by sensing neural activity to provide a input or feedback for the CRM functions. For example, various embodiments record the nerve activity in the cardiac fat pads and use the sensed nerve activity to control the CRM functions. For example, various embodiments sense AV node activity to determine an intrinsic AV delay, allowing the CRM device to use the determined intrinsic AV delay to appropriately time pacing pulses.

The programmer 722 and the IMD 721 are capable of wirelessly communicating data and instructions. In various embodiments, for example, the programmer 722 and IMD 721 use telemetry coils to wirelessly communicate data and instructions. Thus, the programmer can be used to adjust the programmed therapy provided by the IMD 721, and the IMD can report device data, such as battery and lead resistance, and therapy data, such as sense and stimulation data, to the programmer using radio telemetry, for example.

The IMD includes cardiac stimulation capabilities, such as pacing, CRT and defibrillating capabilities. According to various embodiments, the IMD 721 includes a sensor to sense ANS activity. Such a sensor can be used to provide nerve traffic feedback in a closed loop control system. In addition to sensing nerve traffic, various IMD embodiments sense surrogate parameters, such as respiration and blood pressure, indicative of ANS activity. According to various embodiments, the IMD 721 stimulates baroreceptors to provide NS therapy such as AHT therapy. Various IMD embodiments use a lead fed through the right ventricle similar to a cardiac pacemaker lead, and further fed into the pulmonary artery to sense and/or stimulate baroreceptor fields. Other embodiments use other baroreceptor sites or baroreflex pathways or combinations thereof, such as illustrated and described with respect to FIGS. 2A-2C, 3 and 4. In some embodiments, the illustrated IMD includes two or more devices capable of communicating with each other via wireless technology; and in some embodiments, the illustrated IMD includes two or more devices capable of communicating with each other via a cable or wire, such as an intravenously fed lead.

Figure 8:
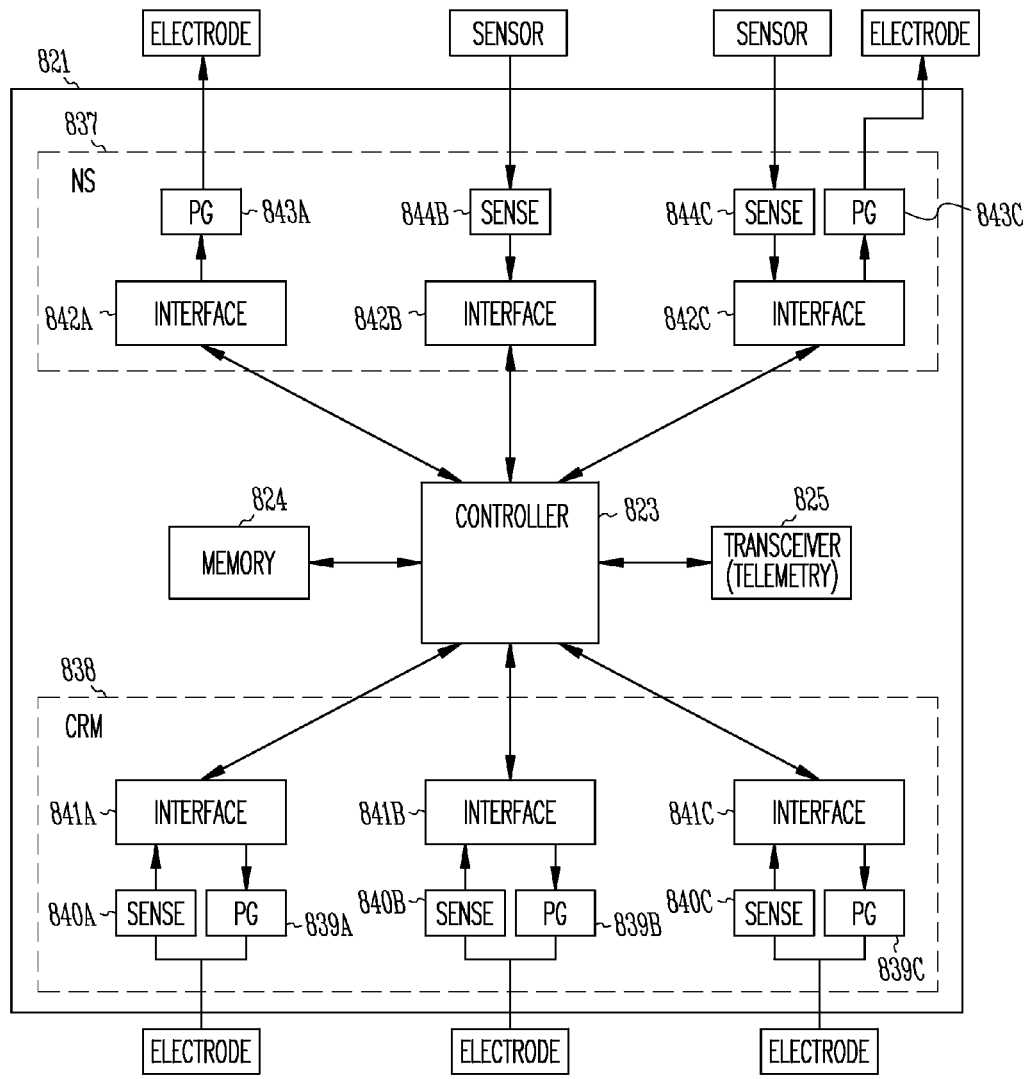
FIG. 8 illustrates an implantable medical device (IMD) such as shown in FIG. 7 having a neural stimulator (NS) component and cardiac rhythm management (CRM) component, according to various embodiments of the present subject matter.

FIG. 8 illustrates an implantable medical device (IMD) such as shown in FIG. 7 having a neural stimulator (NS) component and cardiac rhythm management (CRM) component, according to various embodiments of the present subject matter. The illustrated device 821 includes a controller 823 and a memory 824. According to various embodiments, the controller 823 includes hardware, software, or a combination of hardware and software to perform the neural stimulation and CRM functions. Examples of CRM functions include, for example, pacing, defibrillating, and CRT functions. For example, the programmed therapy applications discussed in this disclosure are capable of being stored as computer-readable instructions embodied in memory and executed by a processor. According to various embodiments, the controller 823 includes a processor to execute instructions embedded in memory to perform the CRM functions and neural sensing functions. Some embodiments further include neural stimulation functions. The illustrated device 821 further includes a transceiver 825 and associated circuitry for use to communicate with a programmer or another external or internal device. Various embodiments include a telemetry coil.

The CRM therapy section 838 includes components, under the control of the controller, to stimulate a heart and/or sense cardiac signals using one or more electrodes. The CRM therapy section includes a pulse generator(s) 839A-C for use to provide an electrical signal through electrodes to stimulate a heart, and further includes sense circuitry 840A-C to detect and process sensed cardiac signals or otherwise detect pulsatile parameters according to the present subject matter. An interface(s) 841A-C is generally illustrated for use to communicate between the controller 823 and the pulse generator(s) 839A-C and sense circuitry 840A-C. Three electrodes are illustrated as an example for use to provide CRM therapy. However, the present subject matter is not limited to a particular number of electrode sites. One or more electrodes can be positioned on a lead, and one or more leads can be used. Each electrode may include its own pulse generator and sense circuitry. However, the present subject matter is not so limited. The pulse generating and sensing functions can be multiplexed to function with multiple electrodes.

The NS therapy section 837 includes components, under the control of the controller, to sense nerve traffic, such as ANS parameters associated with nerve activity, and in some embodiments to stimulate nerves and/or to sense surrogates of ANS parameters such as blood pressure and respiration. Examples of NS therapy include, but are not limited to, therapies to treat hypertension, epilepsy, obesity and breathing disorders. Three interfaces 842A-C are illustrated. However, the present subject matter is not limited to a particular number interfaces, or to any particular stimulating or sensing functions. Pulse generators 843A and 843C are used to provide electrical pulses to an electrode for use to stimulate a site, such as a baroreceptor site to achieve a baroreflex response or a chemoreceptor site. According to various embodiments, the pulse generator includes circuitry to set, and in some embodiments change, the amplitude of the stimulation pulse, the frequency of the stimulation pulse, the burst frequency of the pulse, and/or the morphology of the pulse such as a square wave, triangle wave, sinusoidal wave, and waves with desired harmonic components to mimic white noise or other signals. Sense circuits 844B and 844C are used to detect and process signals from a sensor, such as a sensor of nerve activity. Various embodiments further include sensors of pulsatile parameters, blood pressure, respiration, and the like. The interfaces 842A-C are generally illustrated for use to communicate between the controller 823 and the pulse generator(s) 843A and 843C and sense circuitry 844B and 844C. Each interface, for example, may be used to control a separate lead. Other configurations are possible. For example, interface functions can be multiplexed to control a number of leads. Various embodiments of the NS therapy section only include a pulse generator to stimulate baroreceptors. Embodiments of the CRM therapy section modify therapy based on data received from the NS therapy section, such as nerve traffic data. Some embodiments further modify CRM therapy based on other parameters such as mean arterial pressure, systolic and diastolic pressure, and baroreflex stimulation rate.

According to various embodiments, the lead(s) and the electrode(s) on the leads are physically arranged with respect to the heart in a fashion that enables the electrodes to properly transmit pulses and sense signals from the heart, and with respect to baroreceptors, such as nerve endings and nerve trunks, to sense nerve traffic and in some embodiments to stimulate the baroreflex. As there may be a number of leads and a number of electrodes per lead, the configuration can be programmed to use a particular electrode or electrodes.

Figure 9:
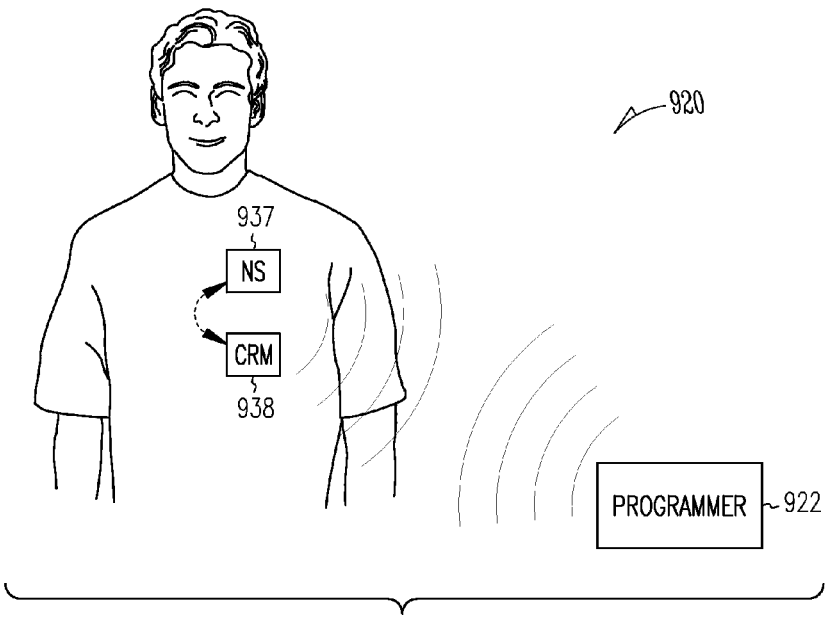
FIG. 9 illustrates a system including a programmer, an implantable neural stimulator (NS) device and an implantable cardiac rhythm management (CRM) device, according to various embodiments of the present subject matter.

FIG. 9 illustrates a system 920 including a programmer 922, an implantable neural stimulator (NS) device 937 and an implantable cardiac rhythm management (CRM) device 938, according to various embodiments of the present subject matter. Various aspects involve a method for communicating between an NS device 937, such as an AHT device, and a CRM device 938 or other cardiac stimulator. In various embodiments, this communication allows one of the devices 937 or 938 to deliver more appropriate therapy (i.e. more appropriate NS therapy or CRM therapy) based on data received from the other device. Some embodiments provide on-demand communications. In various embodiments, this communication allows each of the devices 937 and 938 to deliver more appropriate therapy (i.e. more appropriate NS therapy and CRM therapy) based on data received from the other device. The illustrated NS device 937 and the CRM device 938 are capable of wirelessly communicating with each other, and the programmer is capable of wirelessly communicating with at least one of the NS and the CRM devices 937 and 938. For example, various embodiments use telemetry coils to wirelessly communicate data and instructions to each other. In other embodiments, communication of data and/or energy is by ultrasonic means.

In some embodiments, the NS device 937 senses ANS activity, and in some embodiments, the NS device also stimulates the baroreflex to provide NS therapy. The CRM device 938 includes cardiac stimulation capabilities, such as pacing and/or defibrillating capabilities. Some CRM device embodiments provide CRT functions. Rather than providing wireless communication between the NS and CRM devices 937 and 938, various embodiments provide a communication cable or wire, such as an intravenously-fed lead, for use to communicate between the NS device 937 and the CRM device 938.

Figure 10:
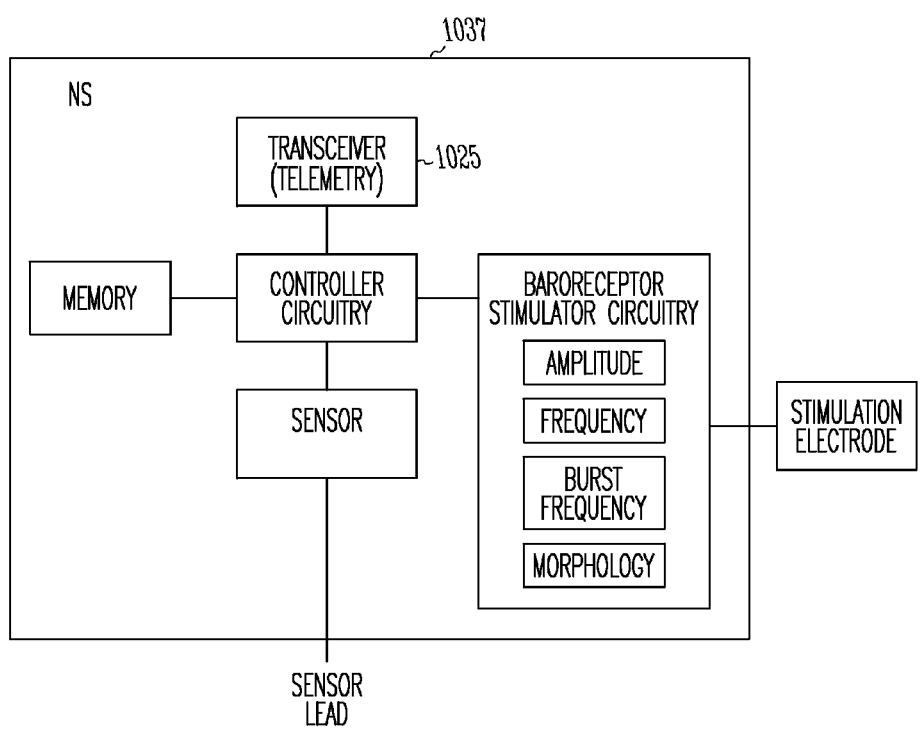
FIG. 10 illustrates an implantable neural stimulator (NS) device such as shown in the system of FIG. 9, according to various embodiments of the present subject matter.
Figure 11:
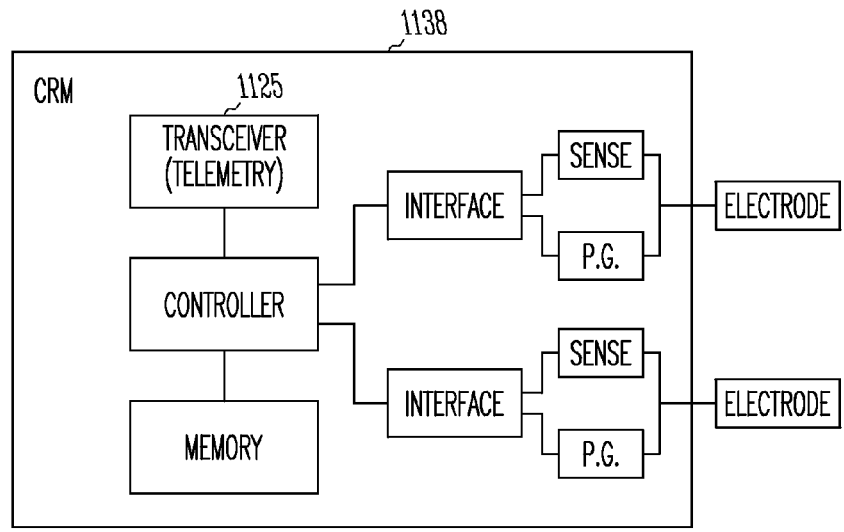
FIG. 11 illustrates an implantable cardiac rhythm management (CRM) device such as shown in the system of FIG. 9, according to various embodiments of the present subject matter.

FIG. 10 illustrates an implantable neural stimulator (NS) device 1037 such as shown at 937 in the system of FIG. 9, according to various embodiments of the present subject matter. In various embodiments, an implantable nerve traffic sensor without neural stimulation capabilities is substituted for the device 1037. FIG. 11 illustrates an implantable cardiac rhythm management (CRM) device 1138 such as shown at 938 in the system of FIG. 9, according to various embodiments of the present subject matter. Functions of the components for the NS device 1037 were previously discussed with respect to the NS component 837 in FIG. 8, and functions of the components for the CRM device 1038 were previously discussed with respect to the CRM component 838 in FIG. 8. In the interest of brevity, these discussions with respect to the NS and CRM functions are not repeated here. Various embodiments of the NS and CRM devices include wireless transceivers 1025 and 1125, respectively, to wirelessly communicate with each other. Various embodiments of the NS and CRM devices include a telemetry coil or ultrasonic transducer to wirelessly communicate with each other.

The CRM device modifies therapy based on data received from the NS device, such as sensed nerve traffic. Various CRM device embodiments further modify therapy based on other data received from the NS device, such as mean arterial pressure, systolic and diastolic pressure, and baroreceptors stimulation rate. Various CRM device embodiments perform CRT functions. Various NS device embodiments are adapted to modify therapy based on electrophysiological parameters received from the CRM device such as heart rate, minute ventilation, atrial activation, ventricular activation, and cardiac events. The functionality of two or more implanted devices is enhanced by providing communication capabilities between or among the implanted devices. In various embodiments, the functionality is further enhanced by designing the devices to wirelessly communicate with each other.

Figure 12:
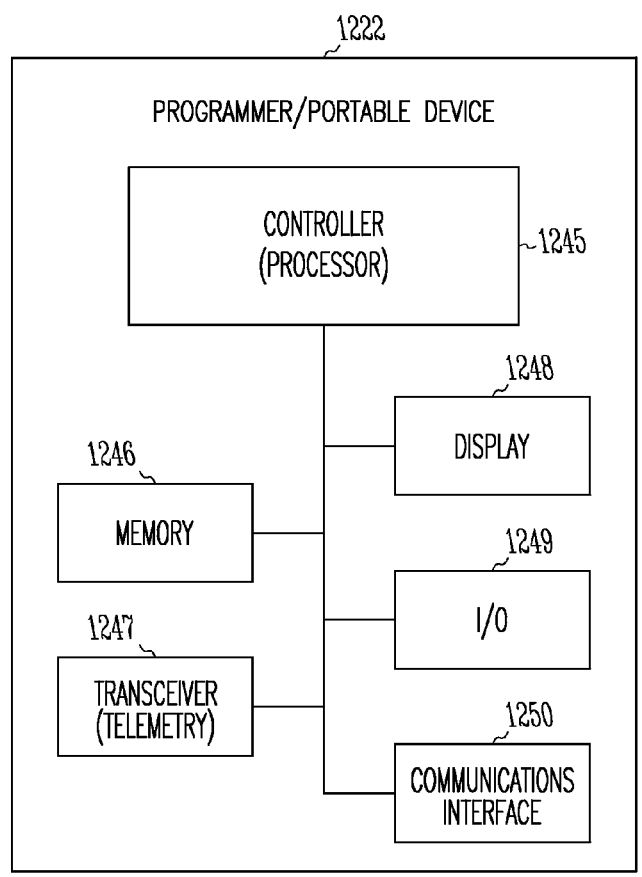
FIG. 12 illustrates a programmer, such as the programmer illustrated in the systems of FIG. 7, or other external device to communicate with the implantable medical device(s), illustrated in FIG. 9, according to various embodiments of the present subject matter.

FIG. 12 illustrates a programmer 1222, such as the programmer 722 illustrated in the systems of FIG. 7 and the programmer 922 illustrated in the system of FIG. 9, or other external device to communicate with the implantable medical device(s), according to various embodiments of the present subject matter. An example of another external device includes Personal Digital Assistants (PDAs) or personal laptop and desktop computers in an Advanced Patient Management (APM) system. The illustrated device 1222 includes controller circuitry 1245 and a memory 1246. The controller circuitry 1245 is capable of being implemented using hardware, software, and combinations of hardware and software. For example, according to various embodiments, the controller circuitry 1245 includes a processor to perform instructions embedded in the memory 1246 to perform a number of functions, including communicating data and/or programming instructions to the implantable devices. The illustrated device 1222 further includes a transceiver 1247 and associated circuitry for use to communicate with an implantable device. Various embodiments have wireless communication capabilities. For example, various embodiments of the transceiver 1247 and associated circuitry include a telemetry coil for use to wirelessly communicate with an implantable device. The illustrated device 1222 further includes a display 1248, input/output (I/O) devices 1249 such as a keyboard or mouse/pointer, and a communications interface 1250 for use to communicate with other devices, such as over a communication network.

The above-described functions of a system, whether implemented in two separate and distinct implantable devices or integrated as components into one or more implantable devices, includes, but is not limited to, processes for monitoring nerve traffic as part of a closed-loop neural stimulation system to continuously deliver appropriate neural stimulation. Processes can be performed by a processor executing computer-readable instructions embedded in memory, for example.

The present subject matter provides CRM therapy with nerve traffic feedback using lead(s) that can be used to detect and monitor nerve traffic. The lead is adapted to be connected to a device, such as an implantable CRM device. The device processes the nerve signal with appropriate amplification and filtering for the low amplitude and high noise level associated with the nerve signal. Various embodiments provide a signal processing module that can include a wavelet transformation or other noise reduction algorithm. Recorded nerve traffic is processed with a detection algorithm adapted to identify the features of the signal, such as the pattern and intensity of the nerve traffic. The signal features are used to determine desired parameters of CRM therapy.

A lead to sense nerve traffic can be placed in a number of appropriate locations. For example, various lead embodiments are expandable, and are adapted to be placed in the pulmonary artery in the proximity of a high concentration of baroreceptors. Various lead embodiments are adapted to sense nerve endings in cardiac fat pads. Some lead embodiments are transvascular leads placed proximal to a cardiac fat pad. Some lead embodiments place an epicardial lead in a cardiac fat pad. Various lead embodiments include a cuff electrode adapted to be placed around a nerve, such as the aortic, carotid or vagus nerve. Other leads can be placed in other neural sensing locations for use in monitoring nerve traffic to provide feedback for CRM therapy. Various device embodiments monitor and record autonomic nerve traffic data as part of an APM system.

Figure 13:
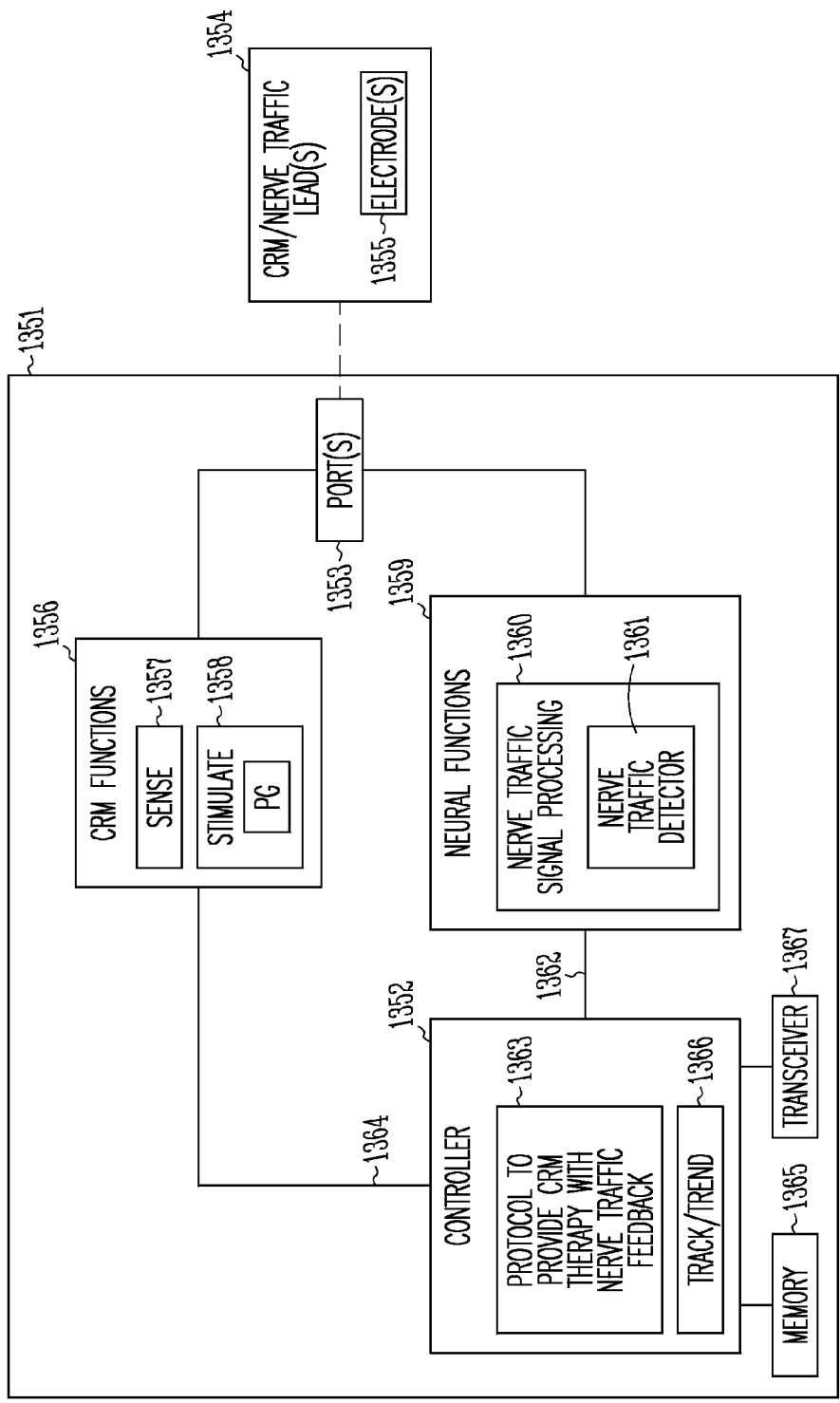
FIG. 13 illustrates an IMD device adapted to provide CRM therapy with nerve traffic feedback, according to various embodiments of the present subject matter.

FIG. 13 illustrates an IMD device adapted to provide CRM therapy with nerve traffic feedback, according to various embodiments of the present subject matter. The illustrated device 1351 includes a controller 1352 and at least one port 1353. Each port is adapted to be connected to a lead 1354, the connection being illustrated by the dotted line. Each lead includes at least one electrode 1355. CRM therapy and nerve traffic sensing are performed using one or more leads. For example, various embodiments use the same lead to apply stimulation signals to capture cardiac tissue for pacing or defibrillation, to sense electrogram signals from the heart, and to sense nerve traffic. These functions are capable of being performed using the same electrode on the lead, to use different electrodes on the same lead, or to use electrodes on different leads. Various embodiments use different electrodes to sense nerve traffic and to perform the CRM therapy.

The illustrated IMD device 1351 includes a CRM functions module 1356 to perform CRM functions, including sense functions 1357 and stimulate functions 1358. The CRM function module is illustrated between the port(s) and the controller. The CRM functions are capable of being performed by the CRM therapy section 838 illustrated in FIG. 8, for example. The present subject matter is not so limited.

Figure 17:
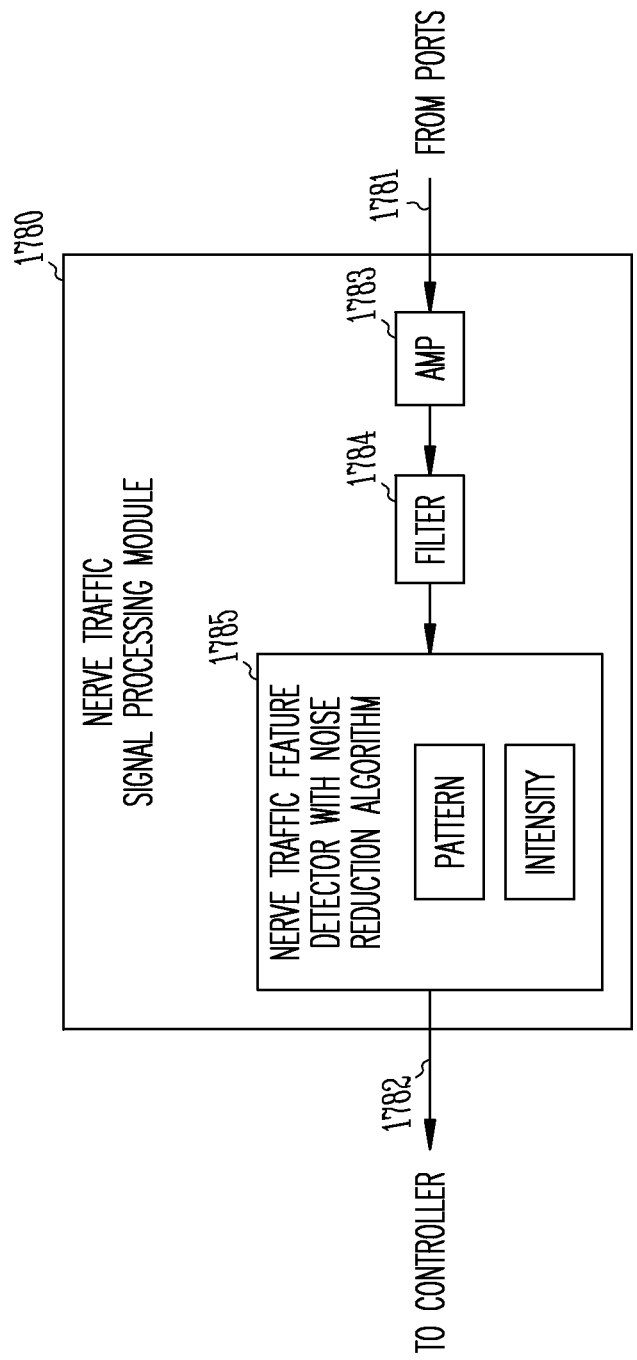
FIG. 17 illustrates a nerve traffic signal processing module, according to various embodiments of the present subject matter.

The illustrated IMD device 1351 includes a neural functions module 1359 to perform neural functions, including a module 1360 to process nerve traffic signals from at least one electrode on at least one lead. The neural functions module is illustrated between the controller and the port(s). Various embodiments of the neural functions module 1359 include a nerve traffic detector 1361 to detect a nerve traffic parameter corresponding to a nerve traffic pattern, various embodiments detect a nerve traffic parameter corresponding to nerve traffic intensity, and various embodiments detect a nerve traffic parameter corresponding to a nerve traffic pattern and a nerve traffic intensity. Various embodiments of the neural functions module include a nerve traffic signal processing module such as is illustrated in FIG. 17.

The controller 1352 is adapted to receive a signal indicative of nerve traffic via signal path 1362 from the neural function module 1359, to implement a protocol 1363 to provide CRM therapy with nerve traffic feedback, and to control the CRM functions module 1356 via signal path 1364. Thus, according to various embodiments, for example, the controller is adapted to adjust CRM therapy based on a detected nerve traffic pattern and/or a detected nerve intensity.

The illustrated device 1351 further includes a memory 1365. In various embodiments, the controller is adapted to store nerve traffic data in the memory, and to track or trend the nerve traffic data using the track/trend module 1366 to further guide the CRM therapy. The illustrated device 1351 further includes a transceiver 1367 to communicate with the controller for use to communicate with another IMD, a programmer, or an advanced patient management (APM) device.

Functions performed by the illustrated modules can be implemented using hardware, software, and a combination of software and hardware. Logical changes can be made such that the functions can be logically grouped in other modules or to form different modules. For example, in various embodiments, the controller includes the hardware and/or software to detect the nerve traffic.

Figure 14:
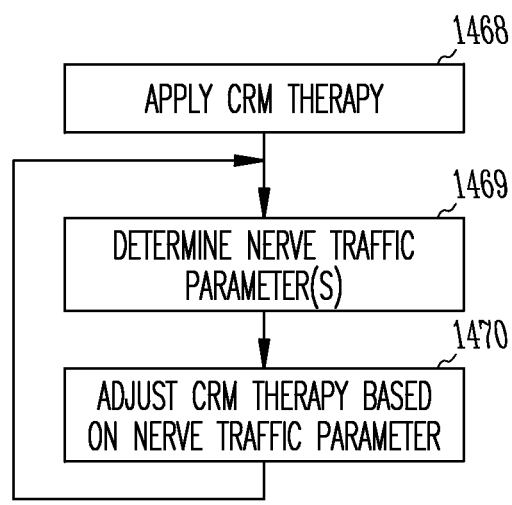
FIG. 14 illustrates a method performed by the IMD device of FIG. 13, according to various embodiments of the present subject matter.

FIG. 14 illustrates a method performed by the IMD device of FIG. 13, according to various embodiments of the present subject matter. At 1468, CRM therapy is applied. For example, various embodiment apply the CRM therapy using the CRM function module 1356 under the control of the controller 1352, such as illustrated in FIG. 13. Various embodiments apply CRT as a CRM therapy. At 1469, at least one nerve traffic parameter is determined. For example, various embodiments determine the nerve traffic parameter using the neural functions module 1359, and provide a signal indicative of the at least one nerve traffic parameter via signal path 1362, such as illustrated in FIG. 13. At 1470, the CRM therapy is adjusted based on the nerve traffic parameter. The nerve traffic is affected by the applied CRM therapy, such that the sensed nerve traffic parameter provides a closed loop feedback for the CRM therapy. For example, various embodiments receive the signal indicative of the sensed nerve traffic at the controller 1352, which implements the protocol 1363 to adjust the CRM therapy based on the nerve traffic parameter.

Figure 15:
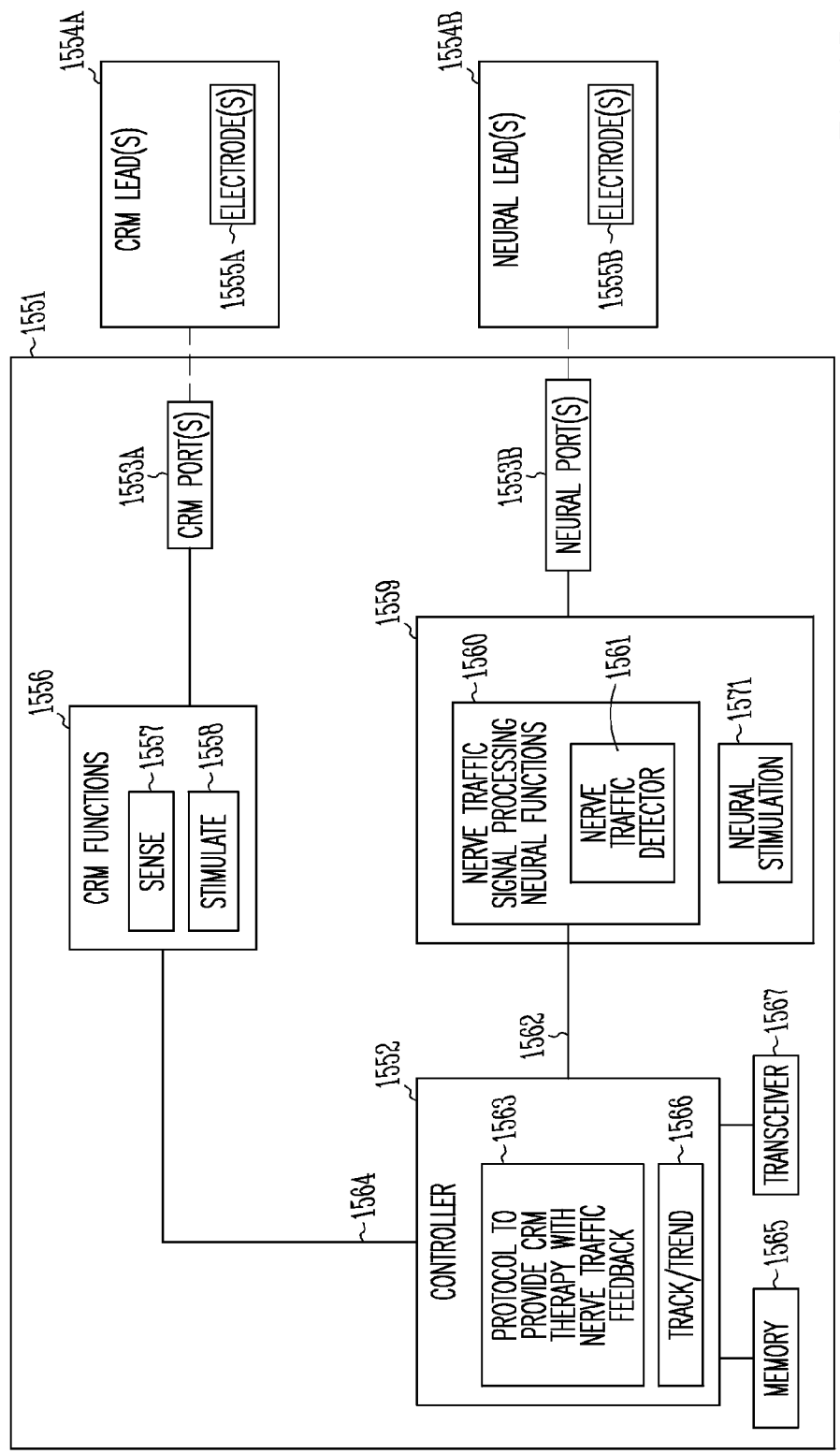
FIG. 15 illustrates an IMD device adapted to provide CRM therapy with nerve traffic feedback and to provide neural stimulation, according to various embodiments of the present subject matter.

FIG. 15 illustrates an IMD device adapted to provide CRM therapy with nerve traffic feedback and to provide neural stimulation, according to various embodiments of the present subject matter. The illustrated device 1551 includes a controller 1552 and at least one port 1553A and 1553B. Each port is adapted to be connected to a lead 1554A and 1554B. Each lead includes at least one electrode 1555A, 1555B. CRM therapy and nerve traffic sensing are performed using one or more leads. For example, various embodiments use the same lead to apply stimulation signals to capture cardiac tissue for pacing or defibrillation, to sense electrogram signals from the heart, and to sense nerve traffic. These functions are capable of being performed using the same electrode on the lead, to use different electrodes on the same lead, or to use electrodes on different leads. Various embodiments use different electrodes to sense nerve traffic and to perform the CRM therapy. The illustrated device includes CRM port(s) 1553A to connect lead(s) 1554A for use to perform CRM therapy, and includes neural port(s) 1553B to connect lead(s) 1554B for use to perform neural sensing.

The illustrated IMD device 1551 includes a CRM functions module 1556 to perform CRM functions, including sense functions 1557 and stimulate functions 1558. The CRM function module is illustrated between the port(s) and the controller. The CRM functions are capable of being performed by the CRM therapy section 838 illustrated in FIG. 8, for example. The present subject matter is not so limited.

The illustrated IMD device includes a neural functions module 1559 to perform neural functions, including processing nerve traffic signals 1560 from at least one electrode on at least one lead. The neural functions module is illustrated between the controller and the port(s). Various embodiments of the neural functions module include a nerve traffic detector 1561 to detect a nerve traffic parameter corresponding to a nerve traffic pattern, various embodiments detect a nerve traffic parameter corresponding to nerve traffic intensity, and various embodiments detect a nerve traffic parameter corresponding to a nerve traffic pattern and a nerve traffic intensity. Various embodiments of the neural functions module include a nerve traffic signal processing module such as is illustrated in FIG. 17. Various embodiments of the neural functions module further provide neural stimulation 1571 to at least one electrode on at least one lead through the neural port(s). Neural stimulation is capable of being implemented as part of a desired neural stimulation therapy, such as an AHT therapy, for example. Additionally, in view of a tendency of nerves to adapt (and thus no longer react or be less sensitive to a stimulus), the neural stimulation can be applied to perturb the system in preparation for determine a nerve traffic response.

The controller is adapted to receive a signal indicative of nerve traffic via signal path 1562, to implement a protocol 1563 to provide CRM therapy with nerve traffic feedback, and to control the CRM functions module via signal path 1564. Thus, according to various embodiments, for example, the controller is adapted to adjust CRM therapy based on a detected nerve traffic pattern and/or a detected nerve intensity. The illustrated system is able to perturb the system prior to detecting the nerve traffic parameter(s) to address an ability of the nerves to quickly adapt to changes. According to various embodiments, the controller provides a signal to the neural stimulations module to provide a stimulation signal before detecting the nerve traffic parameter(s).

The illustrated device further includes a memory 1565. In various embodiments, the controller is adapted to store nerve traffic data in the memory, and to track or trend the nerve traffic data using the track/trend module 1566 to further guide the CRM therapy. The illustrated device further includes a transceiver 1567 to communicate with the controller for use to communicate with another IMD, a programmer, or an advanced patient management (APM) device.

Figure 16:
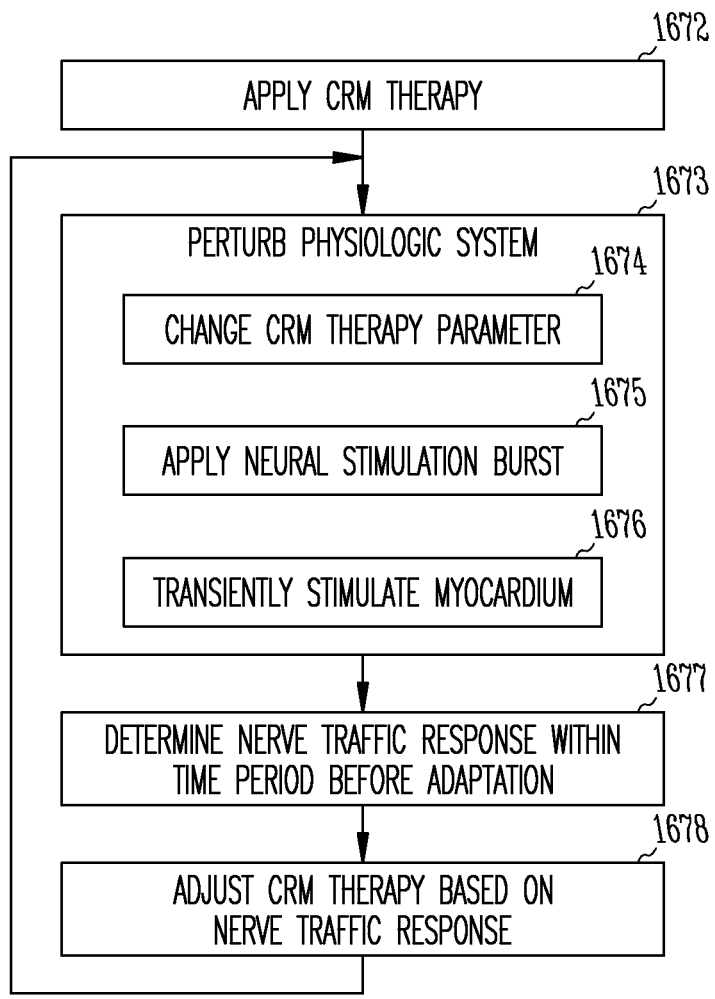
FIG. 16 illustrates a method performed by the IMD device of FIG. 15, according to various embodiments of the present subject matter.

FIG. 16 illustrates a method performed by the IMD device of FIG. 15, according to various embodiments of the present subject matter. At 1672, CRM therapy is applied. For example, various embodiment apply the CRM therapy using the CRM function module under the control of the controller, such as illustrated in FIG. 15. At 1673, the physiologic system is perturbed. Various embodiments change a CRM therapy parameter 1674 to perturb the system. For example, various controller embodiments are adapted to send a signal to the CRM functions module to modulate or otherwise change the applied CRM therapy. Various embodiments apply a neural stimulation burst 1675 to perturb the system. For example, various controller embodiments are adapted to send a signal to the neural functions module to apply, modulate or otherwise change neural stimulation. Various embodiments transiently stimulate the myocardium 1676 to perturb the system. For example, various controller embodiments are adapted to send a signal to the CRM functions module to transiently stimulate the myocardium.

At 1677, at least one nerve traffic parameter is determined within a time period before the nerve traffic adapts to the perturbed system. Various embodiments monitor the nerve traffic and quickly determine a response after the physiologic system is perturbed. For example, the nerve traffic response time is less than 100 ms. Thus, the nerve traffic is monitored to determine a reaction to perturbing the system. For example, various embodiments determine the nerve traffic parameter using the illustrated neural functions module, and provide a signal indicative of the at least one nerve traffic parameter, such as illustrated in FIG. 15. At 1678, the CRM therapy is adjusted based on the nerve traffic parameter. The nerve traffic is affected by the applied CRM therapy, such that the sensed nerve traffic parameter provides a closed loop feedback for the CRM therapy. For example, various embodiments receive the signal indicative of the sensed nerve traffic at the controller, which implements the protocol to adjust the CRM therapy based on the nerve traffic parameter.

FIG. 17 illustrates a nerve traffic signal processing module, according to various embodiments of the present subject matter. In various embodiments, the illustrated signal processing module 1780 is included in the neural functions module in FIGS. 14 and 15. The illustrated signal processing module 1780 is adapted to receive a nerve traffic signal via path 1781 and port(s) from lead(s) and to provide a signal indicative of the nerve traffic via path 1782 to the controller. Various embodiments include an amplifier 1783 and filter 1784 adapted to process the nerve activity into a signal conditioned for discrimination or other processing. Various amplifier embodiments provide a gain within a range of approximately 1,000 to 99,000. Various filter embodiments pass frequencies in a range from approximately 30 Hz to approximately 3,000 Hz. The illustrated signal processing module further includes a nerve traffic feature detector 1785, also referred to as a discriminator, to process the amplified and filtered signal to provide a signal indicative of the nerve traffic to the controller. Various embodiments implement a noise reduction algorithm, such as a wavelet transformation, for use in discriminating the signal. Various embodiments of the nerve traffic feature detector discriminate a noise traffic pattern feature and/or a noise traffic intensity feature; and send these signals to the controller for use to guide the CRM therapy.

Figure 18:
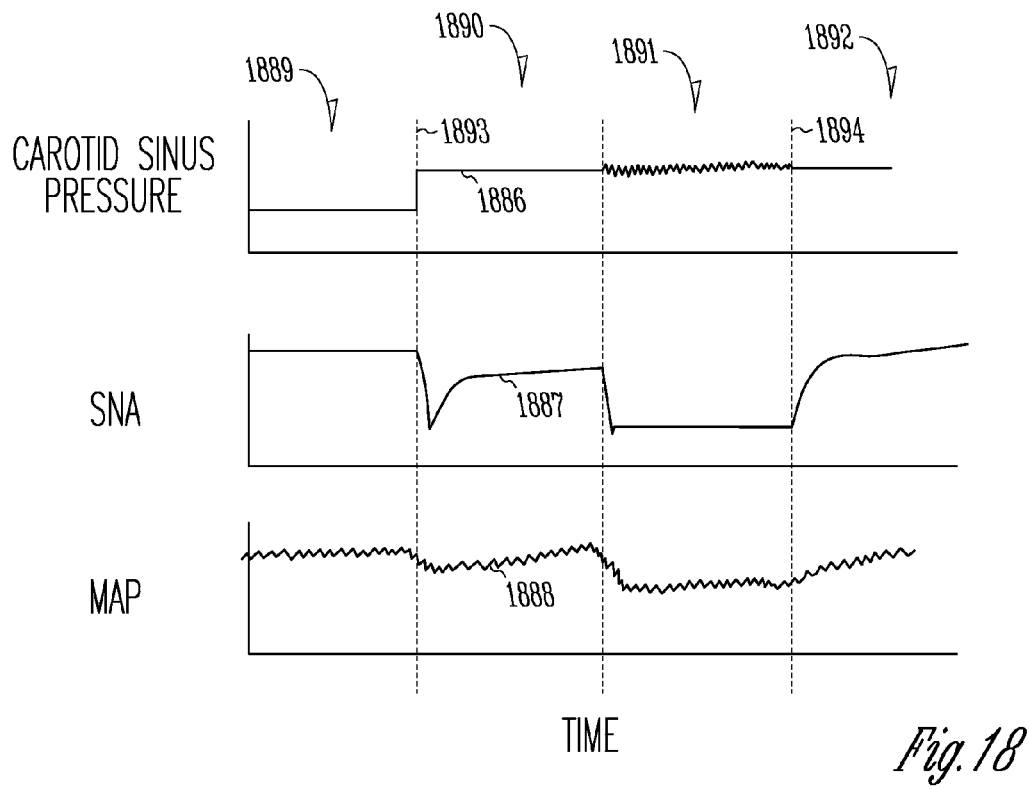
FIG. 18 illustrates baroreflex adaptation using a relationship between carotid sinus pressure, sympathetic nerve activity (SNA) and mean arterial pressure (MAP).

The baroreflex adapts to increased baroreceptor stimulation. Thus, baroreflex adaptation poses a problem for sustaining baroreflex therapy that effectively inhibits SNA. FIG. 18 illustrates baroreflex adaptation using a relationship between carotid sinus pressure 1886, sympathetic nerve activity (SNA) 1887 and mean arterial pressure (MAP) 1888. Internal pressure and stretching of the arterial wall, such as that which occurs at the carotid sinus, naturally activates the baroreflex and the baroreflex inhibits SNA. The carotid sinus pressure, the SNA and the MAP are illustrated for the following four time segments: (1) relatively low and constant carotid sinus pressure 1886 indicated at 1889; (2) relatively high and constant carotid sinus pressure 1886 indicated at 1890; (3) relatively high and pulsed carotid sinus pressure 1886 indicated at 1891; and (4) a return to a relatively high and constant carotid sinus pressure 1886 indicated at 1892.

When the carotid sinus pressure is relatively low and constant, as illustrated at 1889, the SNA is relatively high and constant, and the pulsating MAP is relatively high. When the carotid sinus pressure is increased to a relatively high and constant pressure at transition 1893, the SNA and MAP initially decrease due to the baroreflex and then increases due to the quick adaptation of the baroreflex to the increased carotid sinus pressure. However, when the carotid sinus pressure pulsates similar to naturally-occurring blood pressure pulses, as illustrated at 1891, the SNA and MAP decrease to relatively low levels and are maintained at these relatively low levels. When the carotid sinus pressure changes from a pulsed to constant pressure at transition 1894, the SNA and MAP both increase again due to the adaptation of the baroreflex. The present subject matter modulates the baroreflex stimulation to mimic the effects of the naturally-occurring pulse pressure and prevent baroreflex adaptation.

Figure 19:
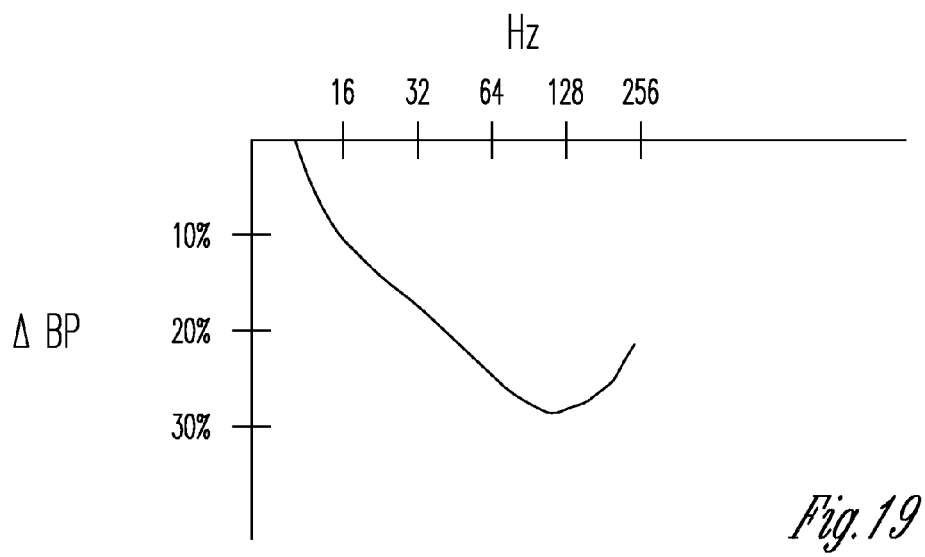
FIG. 19 is a graphical illustration of the relationship between a change in blood pressure and a rate of a stimulation signal.

FIG. 19 is a graphical illustration of the relationship between a change in blood pressure and a rate of a stimulation signal. The figure illustrates that the frequency of the stimulation signal significantly affects the decrease in blood pressure, which is a surrogate baroreflex parameter indicating the inhibition of SNA. The figure illustrates that a maximum decrease in blood pressure occurs at a stimulation frequency within a range from about 64 to about 256 Hz, and occurs approximately at 128 Hz. Various embodiments of the present subject matter periodically modulate the frequency of the stimulation signal to modulate the blood pressure to mimic the effects of a naturally-occurring pulse as generally illustrated at 1891 in FIG. 18. Various embodiments stimulate with a frequency between approximately 8 Hz and approximately 512 Hz, or various ranges within this range such as approximately 16 Hz to approximately 128 Hz, approximately 32 Hz to approximately 128 Hz, for example. Other embodiments modulate other parameters of the stimulation signal to mimic the effects of the naturally-occurring pulse, and thus prevent or reduce baroreflex adaptation. By preventing the baroreflex from adapting to increased baroreceptor activity, long-term baroreceptor stimulation can be used to achieve reflex reduction in hypertension. Periodic baroreceptor stimulation mimics the effect of pulsatile pressure, maintains the reflex inhibition of SNA and prevents adaptation to increased baroreceptor activity that occurs during constant stimulation.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. For example, various embodiments combine two or more of the illustrated processes. Two or more sensed parameters can be combined into a composite parameter used to provide a desired CRM therapy. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An implantable medical device configured to provide a cardiac rhythm management (CRM) therapy to provide a physiologic system with a baseline response and configured to receive feedback from a transient nerve traffic response in a neural target within an autonomic nervous system (ANS), wherein perturbing the physiologic system causes the transient nerve traffic response before nerve traffic at the neural target returns to the baseline response, the device comprising:
    a CRM function module configured to apply the CRM therapy using an electrical signal to capture cardiac tissue, wherein the CRM therapy is configured to provide closed-loop cardiac stimulation to selected chambers of the heart in order to treat disorders of cardiac rhythm;
    a neural function module configured to sense nerve traffic in the neural target within the ANS; and
    a controller connected to the CRM function module and the neural function module, wherein the controller is configured to control the CRM therapy to provide closed-loop cardiac stimulation that causes the baseline response, implement a programmed protocol for receiving the feedback used to control the closed-loop cardiac stimulation, and adjust the CRM therapy using the feedback,
    wherein, in implementing the programmed protocol for receiving the feedback, the controller is configured to:

prepare to determine the transient nerve traffic response by perturbing the physiologic system from the baseline response to cause the transient nerve traffic response to the perturbed system, and determine the transient nerve traffic response to perturbing the physiologic system by monitoring nerve traffic at the neural target within a time period before nerve traffic at the neural target adapts to changes caused by perturbing the physiologic system and returns to the baseline response.

2. The device of claim 1, wherein, in implementing the programmed protocol for receiving the feedback, the controller is configured prepare to determine the transient nerve traffic response by changing a CRM stimulation parameter to cause the transient nerve traffic response.

3. The device of claim 1, wherein, in implementing the programmed protocol for receiving the feedback, the controller is configured prepare to determine the transient nerve traffic response by applying a neural stimulation burst to cause the transient nerve traffic response.

4. The device of claim 1, wherein, in implementing the programmed protocol for receiving the feedback, the controller is configured prepare to determine the transient nerve traffic response by transiently stimulating myocardium.

5. The device of claim 1, wherein the signal indicative of the nerve traffic includes a signal indicative of a nerve traffic pattern, a signal indicative of nerve traffic intensity, or a signal indicative of a nerve traffic pattern and nerve traffic intensity.

6. The device of claim 1, wherein signal processing module is adapted to implement a noise reduction algorithm to identify features of the nerve traffic signal, and the noise reduction algorithm includes a wavelet transformation.

7. The device of claim 1, wherein signal processing module is adapted to implement a noise reduction algorithm to identify features of the nerve traffic signal, and the noise reduction algorithm identifies a pattern and an intensity of the nerve traffic signal.

8. The device of claim 1, wherein the signal processing module includes an amplifier and a filter adapted to process and monitor nerve traffic, wherein the amplifier includes an amplifier with a gain of approximately 1,000 to approximately 99,000, and wherein the filter includes a bandpass filter to pass frequencies in a range from approximately 30 Hz to approximately 3,000 Hz.

9. The device of claim 1, wherein the neural function module is configured to sense nerve traffic from a chemoreceptor that is indicative of a blood gas concentration.

10. The device of claim 1, wherein the neural function module is configured to sense nerve traffic from at least one afferent nerve that is indicative of a blood gas concentration.

11. The device of claim 1, wherein the neural function module is configured to sense nerve traffic from a baroreceptor that is indicative of blood pressure.

12. The device of claim 1, wherein the signal indicative of nerve traffic includes a signal indicative of nerve traffic from at least one afferent nerve that is indicative of blood pressure.

* * * * *